United States Patent
Majima

(10) Patent No.: US 10,370,357 B2
(45) Date of Patent: Aug. 6, 2019

(54) METHOD FOR PRODUCING SULFONYL CHLORIDE COMPOUND

(71) Applicant: TAKEDA PHARMACEUTICAL COMPANY LIMITED, Osaka (JP)

(72) Inventor: Keisuke Majima, Osaka (JP)

(73) Assignee: TAKEDA PHARMACEUTICAL COMPANY LIMITED, Osaka (JP)

( * ) Notice: Subject to any disclaimer, the term of this patent is extended or adjusted under 35 U.S.C. 154(b) by 0 days.

(21) Appl. No.: 15/899,055

(22) Filed: Feb. 19, 2018

(65) Prior Publication Data
US 2018/0170905 A1    Jun. 21, 2018

Related U.S. Application Data

(62) Division of application No. 15/266,307, filed on Sep. 15, 2016, now Pat. No. 9,932,322, which is a division
(Continued)

(30) Foreign Application Priority Data

Feb. 28, 2013 (JP) .................. 2013-039809

(51) Int. Cl.
C07D 401/12 (2006.01)
C07D 213/71 (2006.01)
(Continued)

(52) U.S. Cl.
CPC .......... C07D 401/12 (2013.01); A61K 9/2866 (2013.01); C07D 213/71 (2013.01); A61K 9/2018 (2013.01)

(58) Field of Classification Search
CPC .................................................. C07D 401/12
(Continued)

(56) References Cited

U.S. PATENT DOCUMENTS 4,315,014 A    2/1982 Mich et al.
5,686,486 A    11/1997 Tomich et al.
(Continued)

FOREIGN PATENT DOCUMENTS

EP    0355827 A2    2/1990
EP    0911321 A2    4/1999
(Continued)

OTHER PUBLICATIONS

Cremlyn, Richard J., et al. "Some Reactions of Pyridine-3-Sulfonyl Chloride"; Phosphorus and Sulfur and the Related Elements; vol. 8; 1980; pp. 189-195.

Reinhart, Francis E. "The Preparation of Some N-Substituted 3-Pyridinesulfonamides"; Journal of the Franklin Institute; 236; 1943; pp. 316-320.

Yu, Jing-hua, et al. "Synthesis and Characterization of 2, 6-naphthalenedithiol"; Journal of Beijing University of Chemical Technology; 2005; Vol. 32; No. 3; pp. 89-91.
(Continued)

Primary Examiner — Patricia L Morris
(74) Attorney, Agent, or Firm — Nath, Goldberg & Meyer; Joshua B. Goldberg; Scott H. Blackman

(57) ABSTRACT

An object of the present invention is to provide a production method of an intermediate used in the production method of a sulfonylpyrrole compound useful as a pharmaceutical product. The present invention relates to a method of producing sulfonylpyrrole compound (VI) by reacting a pyridine-3-sulfonic acid compound with phosphorus pentachloride in a solvent of chlorobenzene or trifluoromethylbenzene to give a pyridine-3-sulfonyl chloride compound, reacting the compound without isolation with compound (III) to give compound (IV), and subjecting the compound (IV) to a reductive amination reaction.

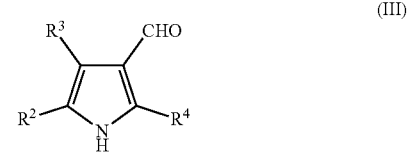

(III)

wherein $R^2$ is a hydrocarbon group etc. and $R^3$ and $R^4$ are each a hydrogen atom etc.,

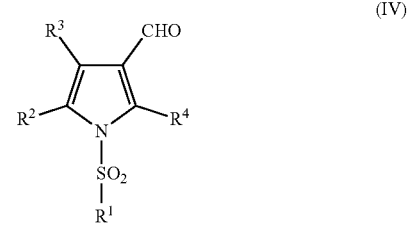
(IV)

wherein $R^2$ is an optionally substituted pyridin-3-yl group, and the other symbols are as defined above,

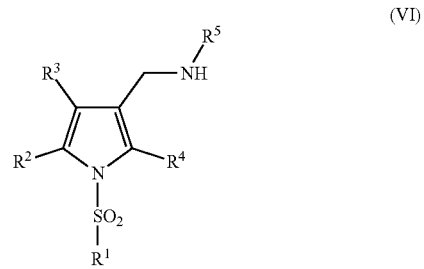
(VI)

wherein $R^5$ is an alkyl group and the other symbols are as defined above.

2 Claims, No Drawings

Related U.S. Application Data of application No. 14/770,914, filed as application No. PCT/JP2014/054808 on Feb. 27, 2014, now Pat. No. 9,487,485.

(51) Int. Cl.
*A61K 9/28* (2006.01)
*A61K 9/20* (2006.01)

(58) Field of Classification Search
USPC .................................................. 546/278.4
See application file for complete search history.

(56) References Cited

U.S. PATENT DOCUMENTS

| | | | |
|---|---|---|---|
| 6,559,167 | B1 | 5/2003 | Garst et al. |
| 8,822,694 | B2 * | 9/2014 | Ikemoto ............ C07D 207/333 546/278.4 |
| 2003/0069299 | A1 | 4/2003 | Walter et al. |
| 2003/0187001 | A1 | 10/2003 | Calderwood et al. |
| 2005/0131042 | A1 | 6/2005 | Flentge et al. |
| 2006/0013799 | A1 | 1/2006 | Konradi et al. |

FOREIGN PATENT DOCUMENTS

| | | |
|---|---|---|
| EP | 2005957 A1 | 12/2008 |
| EP | 2402313 A1 | 1/2012 |
| JP | 2007513067 A | 5/2007 |
| JP | 2010520153 A | 6/2010 |
| JP | 2012501296 A | 1/2012 |
| WO | 9504531 A1 | 2/1995 |
| WO | 9610181 A1 | 4/1996 |
| WO | 9732858 A1 | 9/1997 |
| WO | 9919300 A1 | 4/1999 |
| WO | 9921869 A1 | 5/1999 |
| WO | 0009498 A1 | 2/2000 |
| WO | 0017202 A1 | 3/2000 |
| WO | 0236564 A1 | 5/2002 |
| WO | 03097603 A1 | 11/2003 |
| WO | 2004103968 A1 | 12/2004 |
| WO | 2006033446 A1 | 3/2006 |
| WO | 2006036024 A1 | 4/2006 |
| WO | 2006099972 A1 | 9/2006 |
| WO | 2006127584 A1 | 11/2006 |
| WO | 2007008563 A2 | 1/2007 |
| WO | 2007026916 A1 | 3/2007 |
| WO | 2008003703 A1 | 1/2008 |
| WO | 2008062182 A1 | 5/2008 |
| WO | 2009075806 A1 | 6/2009 |
| WO | 2009144473 A1 | 12/2009 |
| WO | 2010098351 A1 | 9/2010 |
| WO | 2011028741 A1 | 3/2011 |
| WO | 2012110603 A1 | 8/2012 |

OTHER PUBLICATIONS

Arikawa, Yasuyoshi, et al. "Discovery of a Novel Pyrrole Derivitave 1-[5-(2-Fluorophenyl)-1-(pyridin-3-ylsulfonyl)-1H-pyrrol-3-yl]-N-methylmethanamine Fumarate (TAK-438) as a Potassium-Competitive Acid Blocker (P-CAB)"; Journal of Medicinal Chemistry; 2012; vol. 55; pp. 4446-4456.

Egbertson, Melissa S., et al. "Non-Peptide GPIIb/IIIa Inhibitors. 20. Centrally Constrained Thienothiophene a-Sulfonamides Are Potent, Long Acting in Vivo Inhibitors of Platelet Aggregation"; Journal of Medicinal Chemistry; 1999; 42(13); pp. 2409-2421.

Crowell, Thomas A., et al. "3-Sulfonyl-1-carba-1-dethiacephams"; Journal of Medicinal Chemistry; 1989; vol. 32; No. 11; pp. 2436-2442.

Marsais, Francis, et al. "Directed Metalation of Pyridinesulphonamides. Synthesis of Pyridine-fused Isothiazoles and 1,2-Oxathioles"; Journal of Heterocyclic Chemistry; 29 (1); 1992; pp. 61-64.

Karaman, Rafik, et al. "Symmetrical and Unsymmetrical Quadruply Aza Bridged Closely Interspaced Cofacial Bis (5,10,15,20-tetraphenylporphyrin)s. 2. Synthesis, Characterization, and Conformational Effects of Solvents"; Journal of the American Chemical Society; 114(12); 1992; pp. 4889-4898.

Galli, Ubaldina, et al. "Identification of a Sirtuin 3 Inhibitor that Displays Selectivity Over Sirtuin 1 and 2"; European Journal of Medicinal Chemistry; 55; 2012; pp. 58-66.

Bornholdt, Jan, et al. "Ring Opening of Pymisyl-Protected Aziridines with Organocuprates"; Chemistry—A European Journal; 16(41); 2010; pp. 12474-12480.

Owa, Takashi, et al. "Synthesis and Biological Evaluation of N-(7-Indolyl)-3-pyridinesulfonamide Derivatives as Potent Antitumor Agents"; Bioorganic & Medicinal Chemistry Letters; 12(16); 2002; pp. 2097-2100.

Panchaud, Philippe, et al. "3-Pyridinesulfonyl Azide: A Useful Reagent for Radical Azidation"; Advanced Synthesis and Catalysis; vol. 346; No. 8; 2004; pp. 925-928.

International Search Report dated May 13, 2014 corresponding to International application No. PCT/JP2014/054808.

Supplementary European Search Report dated Aug. 1, 2016 corresponding to European application No. EP14757595.

Dorwald, "Side Reactions in Organic Synthesis"; 2005; Wiley:VCH Weinheim Preface; pp. 1-15 & Chapter 8, pp. 279-308.

* cited by examiner

METHOD FOR PRODUCING SULFONYL CHLORIDE COMPOUND

This is a Divisional Application of U.S. patent application Ser. No. 15/266,307, filed Sep. 15, 2016, which was filed as a Divisional Application of U.S. patent application Ser. No. 14/770,914, filed Aug. 27, 2015, an application filed as a national stage under 371 of Application No. PCT/JP2014/054808 filed Feb. 27, 2014 and claiming benefit from Japanese Application No. 2013-039809, filed Feb. 28, 2013, the content of each of which is hereby incorporated by reference in its entirety.

TECHNICAL FIELD

The present invention relates to a production method of a sulfonyl chloride compound used in a production method of a pyrrole compound useful as a pharmaceutical product, particularly an acid secretion inhibitor, and the like.

BACKGROUND OF THE INVENTION

A pyrrole compound having a substituted sulfonyl group at the 1-position (hereinafter to be referred to as a sulfonylpyrrole compound) is useful as an acid secretion inhibitor (proton pump inhibitor), and a therapeutic drug for neoplastic diseases and autoimmune diseases (patent documents 1-3).

For example, patent document 1 describes, as a compound having an acid secretion inhibitory activity, a compound represented by

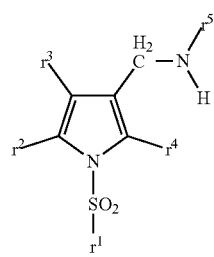

wherein $r^1$ is a monocyclic nitrogen-containing heterocyclic group optionally fused with a benzene ring or heterocycle, and optionally having substituent(s);
$r^2$ is an optionally substituted $C_{6-14}$ aryl group, an optionally substituted thienyl group or an optionally substituted pyridyl group;
$r^3$ and $r^4$ are each a hydrogen atom, or one of $r^3$ and $r^4$ is a hydrogen atom, and the other is an optionally substituted lower alkyl group, an acyl group, a halogen atom, a cyano group or a nitro group; and
$r^5$ is an alkyl group, or a salt thereof.

Patent document 2 describes, as a production method of a sulfonylpyrrole compound, the following method using pyrrole-3-carboxylate ester:

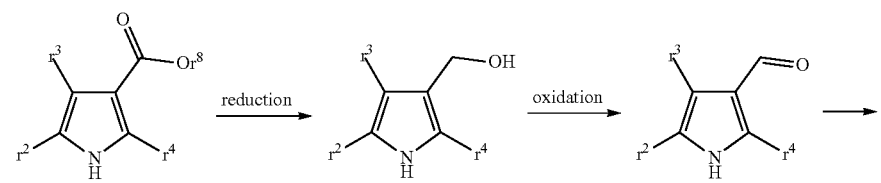

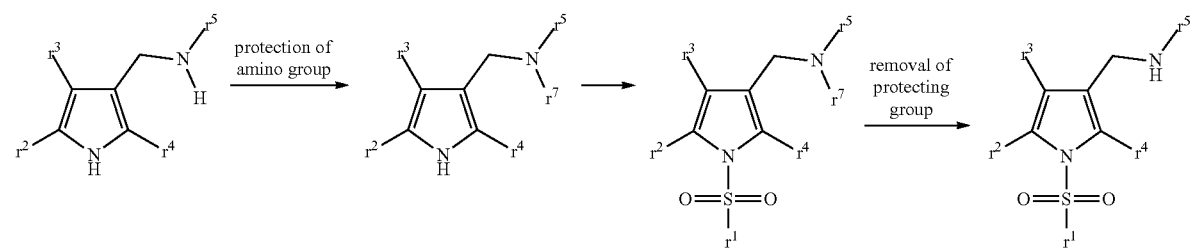

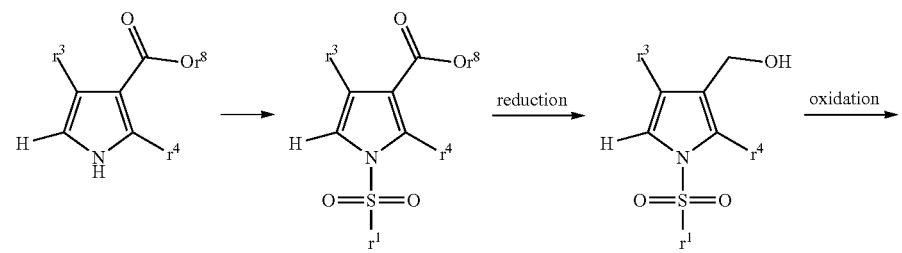

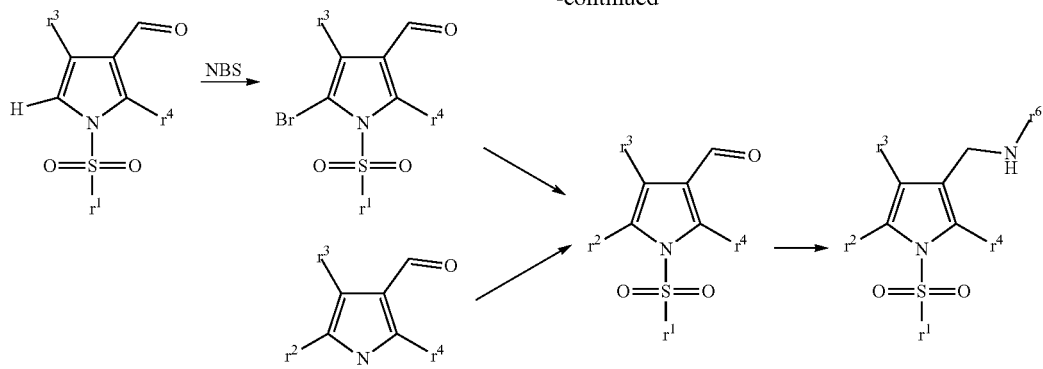

-continued

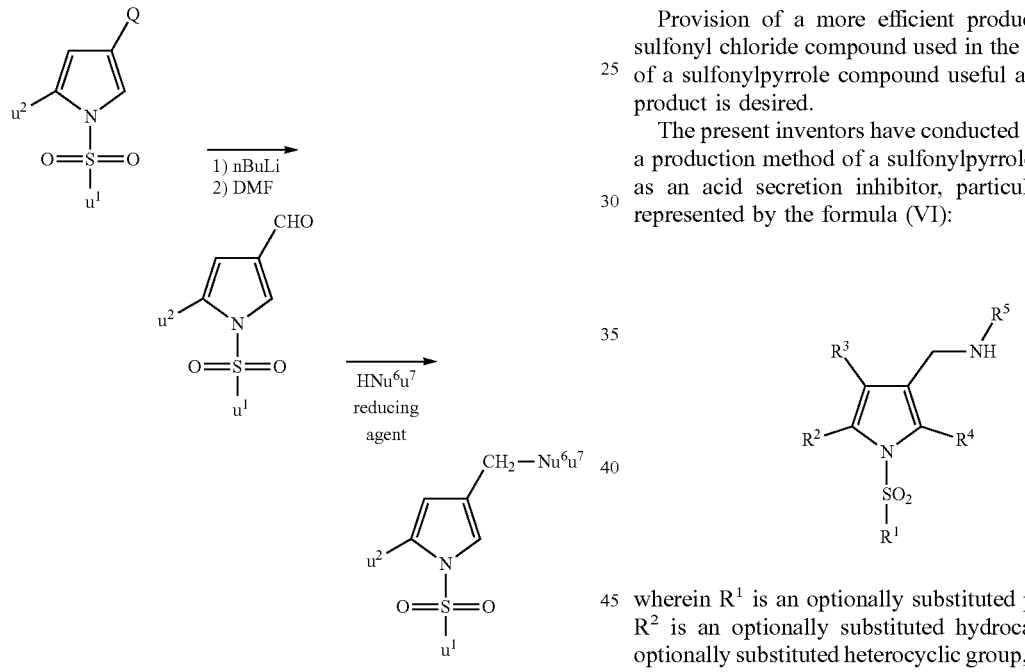

wherein each symbol is as described in patent document 2.

Patent document 3 describes the following production method of a sulfonylpyrrole compound:

wherein each symbol is as described in patent document 3.

Patent documents 4 and 5 describe, as a production method of a sulfonyl chloride compound, a method including reacting pyridine-3-sulfonic acid with phosphorus pentachloride in a solvent of phosphorus oxychloride or toluene to give pyridine-3-sulfonyl chloride. Patent document 6 describes a method including reacting pyridine-3-sulfonic acid with phosphorus pentachloride without solvent to give pyridine-3-sulfonyl chloride.

DOCUMENT LIST

Patent Documents patent document 1: WO2006/036024
patent document 2: WO2007/026916
patent document 3: WO2004/103968
patent document 4: WO2008/003703
patent document 5: WO095/04531
patent document 6: US-B-2003/0069299

SUMMARY OF THE INVENTION

Provision of a more efficient production method of a sulfonyl chloride compound used in the production method of a sulfonylpyrrole compound useful as a pharmaceutical product is desired.

The present inventors have conducted intensive studies of a production method of a sulfonylpyrrole compound useful as an acid secretion inhibitor, particularly, a compound represented by the formula (VI):

(VI)

wherein $R^1$ is an optionally substituted pyridin-3-yl group, $R^2$ is an optionally substituted hydrocarbon group or an optionally substituted heterocyclic group, $R^3$ and $R^4$ are each independently a hydrogen atom, an optionally substituted alkyl group, an acyl group, an optionally substituted hydroxy group, an optionally substituted amino group or a halogen atom, and $R^5$ is an alkyl group, or a salt thereof. As a result, they have found a novel production method of a pyridine-3-sulfonyl chloride compound, which is characterized in that, in a reaction of a pyridine-3-sulfonic acid compound with phosphorus pentachloride to give a pyridine-3-sulfonyl chloride compound, the reaction is performed in a solvent of chlorobenzene or trifluoromethylbenzene, which resulted in the completion of the present invention.

That is, the present invention relates to the following invention.

[1] A production method of a pyridine-3-sulfonyl chloride compound, comprising reacting a pyridine-3-sulfonic acid compound with phosphorus pentachloride in a solvent of chlorobenzene or trifluoromethylbenzene to give the pyridine-3-sulfonyl chloride compound;

[2] a production method of a compound represented by the formula (IV):

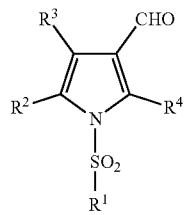
(IV)

wherein $R^1$ is an optionally substituted pyridin-3-yl group, $R^2$ is an optionally substituted hydrocarbon group or an optionally substituted heterocyclic group, and $R^3$ and $R^4$ are each independently a hydrogen atom, an optionally substituted alkyl group, an acyl group, an optionally substituted hydroxy group, an optionally substituted amino group or a halogen atom,
or a salt thereof, comprising reacting, without isolation, the pyridine-3-sulfonyl chloride compound represented by the following formula (II):

$R^1$—$SO_2Cl$ (II)

wherein $R^1$ is as defined above, which is obtained by the production method of the above-mentioned [1],
with a compound represented by the formula (III):

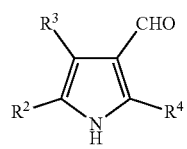
(III)

wherein each symbol is as defined above, or a salt thereof;
[3] a production method of a compound represented by the formula (VI):

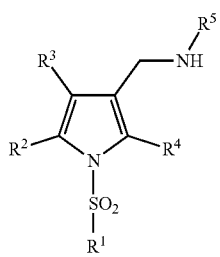
(VI)

wherein $R^1$ is an optionally substituted pyridin-3-yl group, $R^2$ is an optionally substituted hydrocarbon group or an optionally substituted heterocyclic group, $R^3$ and $R^4$ are each independently a hydrogen atom, an optionally substituted alkyl group, an acyl group, an optionally substituted hydroxy group, an optionally substituted amino group or a halogen atom, and $R^5$ is an alkyl group
or a salt thereof, comprising reacting, without isolation, the pyridine-3-sulfonyl chloride compound represented by the following formula (II):

$R^1$—$SO_2$—Cl (II)

wherein $R^1$ is as defined above, which is obtained by the production method of the above-mentioned [1],
with a compound represented by the formula (III):

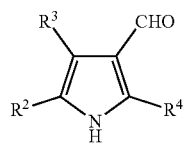
(III)

wherein each symbol is as defined above, or a salt thereof to produce a compound represented by the formula (IV):

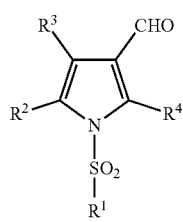
(IV)

wherein each symbol is as defined above,
or a salt thereof, and reacting the compound with a compound represented by the formula (V):

$R^5$—NH2 (V)

wherein $R^5$ is as defined above, or a salt thereof in the presence of a reducing agent;
[4] the production method of the above-mentioned [2] or [3], wherein $R^1$ is an unsubstituted pyridin-3-yl group;
[5] the production method of any of the above-mentioned [2]-[4], wherein $R^2$ is an optionally substituted phenyl group;
[6] the production method of the above-mentioned [2], wherein
$R^1$ is an unsubstituted pyridin-3-yl group,
$R^2$ is a 2-fluorophenyl group, and
$R^3$ and $R^4$ are each a hydrogen atom;
[7] the production method of the above-mentioned [3], wherein
$R^1$ is an unsubstituted pyridin-3-yl group,
$R^2$ is a 2-fluorophenyl group,
$R^3$ and $R^4$ are each a hydrogen atom, and
$R^5$ is a methyl group.

Effect of the Invention

According to the method of the present invention, since the reaction of a pyridine-3-sulfonic acid compound and phosphorus pentachloride to give a pyridine-3-sulfonyl chloride compound is performed in a solvent of chlorobenzene or trifluoromethylbenzene, a treatment (neutralization and distillation operation) of a waste product of phosphorus oxychloride which produces concern about the safety as compared to the above-mentioned conventional methods, can be avoided. In addition, the reaction can be controlled easily and reaction runaway can be suppressed. Thus, a pyridine-3-sulfonyl chloride compound can be obtained conveniently and safely. When toluene is used as a solvent in the above-mentioned reaction, a byproduct is generated. In the method of the present invention, such byproduct is not generated since chlorobenzene or trifluoromethylbenzene is used as a solvent, and a highly pure pyridine-3-sulfonyl chloride compound can be obtained in a high yield. Since the reaction mixture is partitioned and washed, the pyridine-3-sulfonyl chloride compound can be directly used for the next step without isolation, and the sulfonylpyrrole compound can be produced efficiently and conveniently. Furthermore, since the pyridine-3-sulfonyl chloride compound produced from the pyridine-3-sulfonic acid compound is used without isolation, the sulfonylpyrrole compound can be produced at a low cost.

The present invention relates to a production method of a pyridine-3-sulfonyl chloride compound, comprising reacting a pyridine-3-sulfonic acid compound with phosphorus pentachloride in a solvent of chlorobenzene or trifluoromethylbenzene to give the pyridine-3-sulfonyl chloride compound.

As another embodiment of the present invention, by using the pyridine-3-sulfonyl chloride compound obtained by the production method of the present invention without isolation, a sulfonylpyrrole compound useful as an acid secretion inhibitor, particularly a compound represented by the formula (VI):

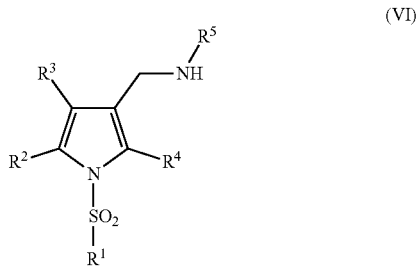

(VI)

wherein $R^1$ is an optionally substituted pyridin-3-yl group, $R^2$ is an optionally substituted hydrocarbon group or an optionally substituted heterocyclic group, $R^3$ and $R^4$ are each independently a hydrogen atom, an optionally substituted alkyl group, an acyl group, an optionally substituted hydroxy group, an optionally substituted amino group or a halogen atom, and $R^5$ is an alkyl group (hereinafter sometimes to be referred to as compound (VI)) or a salt thereof, and an intermediate therefor can be produced efficiently. Compound (VI) and a salt thereof show an extremely strong proton pump inhibitory action. Since compound (VI) and a salt thereof inhibit proton pump ($H^+/K^+$-ATPase) activity reversibly and in a $K^+$ antagonist inhibitory manner, as a result of which suppress acid secretion, they are sometimes referred to as Potassium-Competitive Acid Blocker (P-CAB) or acid pump antagonist (APA). Compound (VI) and a salt thereof show rapid expression of the action and show maximum efficacy from the initial administration. Furthermore, they are characterized in that an influence of metabolic polymorphism (inconsistency among patients) is less, cytotoxicity is low, cytochrome P450 (CYP) inhibitory activity and hERG inhibitory activity are weak, and duration of the action is long. Therefore, compound (VI) and a salt thereof obtained according to the production method of the present invention are useful as clinically useful agents for the prophylaxis or treatment of peptic ulcer (e.g., gastric ulcer, duodenal ulcer, anastomotic ulcer, ulcer caused by non-steroidal anti-inflammatory agent, ulcer due to postoperative stress etc.), Zollinger-Ellison syndrome, gastritis, erosive esopnagitis, reflux esophagitis, symptomatic gastroesophageal reflux disease (Symptomatic GERD), Barrett's esophagus, Functional Dyspepsia, gastric cancer, stomach MALT lymphoma, or hyperacidity; suppressants of recurrence of peptic ulcer, acute stress ulcer, hemorrhagic gastritis, upper gastrointestinal hemorrhage due to invasive stress or ulcer caused by non-steroidal anti-inflammatory agents, and the like. Since compound (VI) and a salt thereof show low toxicity and are superior in water-solubility, in vivo kinetics, and efficacy expression, they are also useful as medicaments. Since compound (VI) and a salt thereof are stable even under acidic conditions, they can be administered orally as normal tablets and the like, without formulating into enteric-coated preparations. Therefore, the preparation such as tablet and the like can be downsized, which advantageously facilitates ingestion for a sick person having a weak ability to swallow, particularly old persons and children. Moreover, since they are free of a sustained release effect of enteric-coated preparations, a gastric acid secretion-inhibiting action is expressed rapidly, and symptoms such as pain and the like are improved rapidly.

DETAILED DESCRIPTION OF THE INVENTION

The definition of each symbol in the formulas is described in detail below.

The "pyridin-3-yl group" of the "optionally substituted pyridin-3-yl group" for $R^1$ may be substituted by 1 to 5 (preferably 1 to 3) substituents selected from (1) a halogen atom, (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atoms (e.g., fluorine atom, chlorine atom, bromine atom, iodine atom) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio (e.g., methylthio, difluoromethylthio, trifluoromethylthio, ethylthio, propylthio, isopropylthio, butylthio, 4,4,4-trifluorobutylthio, pentylthio, hexylthio etc.) optionally having 1 to 3 halogen atoms (e.g., fluorine atom, chlorine atom, bromine atom, iodine atom), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (21) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) aryl-carbamoyl (e.g., phenylcarbamoyl, 1-naphthylcarbamoyl, 2-naphthylcarbamoyl etc.), (30) $C_{1-6}$ alkylsulfonyl (e.g., methylsulfonyl, ethylsulfonyl, trifluoromethylsulfonyl etc.) optionally having 1 to 3 halogen atoms (e.g., fluorine atom, chlorine atom, bromine atom, iodine atom), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ arylcarbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides one nitrogen atom and a carbon atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides carbon atom, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b]furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.), (50) $C_{1-6}$ alkyl group (e.g., methyl, ethyl, n-propyl, isopropyl, n-butyl, isobutyl, sec-butyl, tert-butyl, n-pentyl, sec-pentyl, isopentyl, neopentyl, n-hexyl, isohexyl etc.) optionally having 1 to 3 halogen atoms (e.g., fluorine atom, chlorine atom, bromine atom, iodine atom) or a hydroxy group, (51) $C_{2-6}$ alkenyl group (e.g., allyl, isopropenyl, isobutenvl, 1-methylallyl, 2-pentenyl, 2-hexenyl etc.) optionally having 1 to 3 halogen atoms (e.g., fluorine atom, chlorine atom, bromine atom, iodine atom), (52) a $C_{2-6}$ alkynyl group (e.g., propargyl, 2-butynyl, 3-butynyl, 3-pentynyl, 3-hexynyl etc.), (53) mono-$C_{3-7}$ cycloalkyl-carbamoyl (e.g., cyclopropylcarbamoyl, cyclobutylcarbamoyl etc.), (54) 5- to 10-membered heterocyclyl-carbonyl containing, besides carbon atom, one or two kinds of 1 to 4 hetero atoms selected from a nitrogen atom, a sulfur atom and an oxygen atom, (e.g., 4-morpholinocarbonyl etc.) and the like. These substituents may be bonded to a nitrogen atom of a "pyridin-3-yl group", and are preferably bonded to a carbon atom of a "pyridin-3-yl group".

Examples of the "hydrocarbon group" of the "optionally substituted hydrocarbon group" for $R^2$ include a chain or cyclic hydrocarbon group (e.g., alkyl, alkenyl, alkynyl, cycloalkyl, aryl, aralkyl etc.), Of these, a chain or cyclic hydrocarbon group having 1-16 carbon atoms and the like are preferable.

Examples of "alkyl" include $C_{1-6}$ alkyl (e.g., methyl, ethyl, propyl, isopropyl, butyl, isobutyl, sec-butyl, tert-butyl, pentyl, hexyl etc.) and the like.

Examples of "alkenyl" include $C_{2-6}$ alkenyl (e.g., vinyl, allyl, isopropenyl, 1-butenyl, 2-butenyl, 3-butenyl, 2-methyl-2-propenyl, 1-methyl-2-propenyl, 2-methyl-1-propenyl etc.) and the like.

Examples of "alkynyl" include $C_{2-6}$ alkynyl (e.g., ethynyl, propargyl, 1-butynyl, 2-butynyl, 3-butynyl, 1-hexynyl etc.) and the like.

Examples of "cycloalkyl" include $C_{3-7}$ cycloalkyl (e.g., cyclopropyl, cyclobutyl, cyclopentyl, cyclohexyl, cycloheptyl etc.) and the like.

Examples of "aryl" include $C_{6-14}$ aryl (e.g., phenyl, 1-naphthyl, 2-naphthyl, 2-biphenylyl, 3-biphenylyl, 4-biphenylyl, 2-anthryl etc.) and the like.

Examples of "aralkyl" include $C_{7-16}$ aralkyl (e.g., phenyl-$C_{1-6}$ alkyl such as benzyl, phenethyl, diphenylmethyl, 1-naphthylmethyl, 2-naphthylmethyl, 2,2-diphenylethyl, 3-phenylpropyl, 4-phenylbutyl, 5-phenylpentyl and the like, naphthyl-$C_{1-6}$ alkyl, diphenyl-$C_{1-4}$ alkyl etc.) and the like.

When the above-mentioned hydrocarbon group is alkyl, alkenyl or alkynyl, it may be substituted by 1 to 3 substituents selected from (1) halogen atom (e.g., fluorine atom, chlorine atom, bromine atom, iodine atom etc.), (2) nitro, (3) cyano, (4) hydroxy, (5) $C_{1-6}$ alkoxy (e.g., methoxy, ethoxy, propoxy, isopropoxy, butoxy, isobutoxy, sec-butoxy, pentyloxy, hexyloxy, fluoromethoxy etc.) optionally having 1 to 3 halogen atoms (e.g., fluorine atom, chlorine atom, bromine atom, iodine atom), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., fluorine atom, chlorine atom, bromine atom, iodine atom) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-15}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13) mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenylcarbamoyl, 1-naphthylcarbamoyl, 2-naphtylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.), (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides one nitrogen atom and a carbon atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides a carbon atom, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo [b] furanyl etc.), (48) $C_{1-3}$ alkylenedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like.

In addition, when the above-mentioned hydrocarbon group is cycloalkyl, aryl or aralkyl, it may be substituted by a substituent similar to that of the above-mentioned "pyridin-3-yl group" for $R^1$. The number of the substituents is 1 to 5, preferably 1 to 3.

Examples of the "heterocyclic group" of the "optionally substituted heterocyclic group" for $R^2$ include a 3- to 8-membered heterocyclic group (preferably 5- or 6-membered heterocyclic group) containing 1 to 4 hetero atoms such as a nitrogen atom (optionally oxidized), an oxygen atom, a sulfur atom (optionally mono- or di-oxidized) and the like, a group formed by condensation of a 3- to 8-membered heterocyclic group (preferably 5- or 6-membered heterocyclic group) containing 1 to 4 hetero atoms such as a nitrogen atom (optionally oxidized), an oxygen atom, a sulfur atom (optionally mono- or di-oxidized) and the like and a benzene ring or a 3- to 8-membered heterocyclic group (preferably 5- or 6-membered heterocyclic group) containing 1 to 4 hetero atoms such as a nitrogen atom (optionally oxidized), an oxygen atom, a sulfur atom (optionally mono- or di-oxidized) and the like, preferably a group formed by condensation of the 5- or 6-membered heterocyclic group and a 5- or 6-membered ring optionally containing 1 to 4 hetero atoms such as a nitrogen atom (optionally oxidized), an oxygen atom, a sulfur atom (optionally mono- or di-oxidized) and the like.

To be specific, aziridinyl (e.g., 1- or 2-aziridinyl), aziriryl (e.g., 1- or 2-azirinyl), azetyl (e.g., 2-, 3- or 4-azetyl), azetidinyl (e.g., 1-, 2- or 3-azetidinyl), perhydroazepinyl (e.g., 1-, 2-, 3- or 4-perhydroazepinyl), perhydroazocinyl (e.g., 1-, 2-, 3-, 4- or 5-perhydroazocinyl), pyrrolyl (e.g., 1-, 2- or 3-pyrrolyl), pyrazolyl (e.g., 1-, 3-, 4- or 5-pyrazolyl), imidazolyl (e.g., 1-, 2-, 4- or 5-imidazolyl), triazolyl (e.g., 1,2,3-triazol-1-, 4- or 5-yl, 1,2,4-triazol-1-, 3-, 4- or 5-yl), tetrazolyl (e.g., tetrazol-1-, 2- or 5-yl), furyl (e.g., 2- or 3-furyl), thienyl (e.g., 2- or 3-thienyl), thienyl wherein a sulfur atom is oxidized (e.g., 2- or 3-thienyl-1,1-dioxide), oxazolyl (e.g., 2-, 4- or 5-oxazolyl), isoxazolyl (e.g., 3-, 4- or 5-isoxazolyl), oxadiazolyl (e.g., 1,2,3-oxadiazol-4- or 5-yl, 1,2,4-oxadiazol-3- or 5-yl, 1,2,5-oxadiazol-3-yl, 1,3,4-oxadiazol-2-yl), thiazolyl (e.g., 2-, 4- or 5-thiazolyl), isothiazolyl (e.g., 3-, 4- or 5-isothiazolyl), thiadiazolyl (e.g., 1,2,3-thiadiazol-4- or 5-yl, 1,2,4-thiadiazol-3- or 5-yl, 1,2,5-thiadiazol-3-yl, 1,3,4-thiadiazol-2-yl), pyrrolidinyl (e.g., 1-, 2- or 3-pyrrolidinyl), pyridyl (e.g., 2-, 3- or 4-pyridyl), pyridyl wherein a nitrogen atom is oxidized (e.g., 2-, 3- or 4-pyridyl-N-oxide), pyridazinyl (e.g., 3- or 4-pyridazinyl), pyridazinyl wherein one or both of the nitrogen atoms is/are oxidized (e.g., 3-, 4-, 5- or 6-pyridazinyl-N-oxide), pyrimidinyl (e.g., 2-, 4- or 5-pyrimidinyl), pyrimidinyl wherein one or both of the nitrogen atoms is/are oxidized (e.g., 2-, 4-, 5- or 6-pyrimidinyl-N-oxide), pyrazinyl, piperidinyl (e.g., 1-, 2-, 3- or 4-piperidinyl), piperazinyl (e.g., 1- or 2-piperazinyl), indolyl (e.g., 3H-indol-2-, 3-, 4-, 5-, 6- or 7-yl), pyranyl (e.g., 2-, 3- or 4-pyranyl), thiopyranyl (e.g., 2-, 3- or 4-thiopyranyl), thiopyranyl wherein a sulfur atom is oxidized (e.g., 2-, 3- or 4-thiopyranyl-1,1-dioxide), morpholinyl (e.g., 2-, 3- or 4-morpholinyl), thiomorpholinyl, quinolyl (e.g., 2-, 3-, 4-, 5-, 6-, 7- or 8-quinolyl), isoquinolyl, pyrido[2,3-d]pyrimidinyl (e.g., pyrido[2,3-d]pyrimidin-2-yl), naphthyridinyl such as 1,5-, 1,6-, 1,7-, 1,8-, 2,6- or 2,7-naphthyridinyl and the like (e.g., 1,5-naphthyridin-2- or 3-yl), thieno[2,3-d]pyridyl (e.g., thieno[2,3-d]pyridin-3-yl), pyrazinoquinolyl (e.g., pyrazino[2,3-d]quinolin-2-yl), chromenyl (e.g., 2H-chromen-2- or 3-yl), 2-benzo[b]thienyl, 3-benzo[b]thienyl, 2-benzo[b]furanyl, 3-benzo[b]furanyl, 2,3-dihydro-1-benzofuranyl, 2,1,3-benzothiadiazolyl, 2,3-dihydro-1,4-benzodioxin-5- or -6-yl, 1,3-benzothiazol-6-yl, 1,1-dioxido-2,3-dihydro-1-benzothien-6-yl, 1-benzothienyl and the like.

Examples of the "substituent" of the heterocyclic group include substituents similar to those of the "pyridin-3-yl group" for the above-mentioned $R^1$. The number of the substituents is 1 to 5, preferably 1 to 3.

Examples of the "alkyl group" of the "optionally substituted alkyl group" for $R^3$ or $R^4$ include $C_{1-6}$ alkyl groups such as methyl, ethyl, propyl, isopropyl, butyl, isobutyl, sec-butyl, tert-butyl, pentyl, hexyl and the like, and the like.

Examples of the substituent that the "alkyl group" may have include (1) halogen atom (e.g., fluorine atom, chlorine atom, bromine atom, iodine atom etc.), (2) nitro, (3) cyano, (4) hydroxy, (5) $C_{1-6}$ alkoxy optionally having 1 to 3 halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, fluoromethoxy etc.), (6) $C_{6-14}$ aryloxy (e.g., phenyloxy, naphthyloxy etc.), (7) $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.), (8) mercapto, (9) $C_{1-6}$ alkylthio optionally having 1 to 3 halogen atoms (e.g., fluorine, chlorine, bromine, iodine) (e.g., methylthio, difluoromethylthio, trifluoromethylthio, ethylthio, propylthio, isopropylthio, butylthio, 4,4,4-trifluorobutylthio, pentylthio, hexylthio etc.), (10) $C_{6-14}$ arylthio (e.g., phenylthio, naphthylthio etc.), (11) $C_{7-16}$ aralkylthio (e.g., benzylthio, phenethylthio, diphenylmethylthio, 1-naphthylmethylthio, 2-naphthylmethylthio, 2,2-diphenylethylthio, 3-phenylpropylthio, 4-phenylbutylthio, 5-phenylpentylthio etc.), (12) amino, (13)

mono-$C_{1-6}$ alkylamino (e.g., methylamino, ethylamino etc.), (14) mono-$C_{6-14}$ arylamino (e.g., phenylamino, 1-naphthylamino, 2-naphthylamino etc.), (15) mono-$C_{7-16}$ aralkylamino (e.g., benzylamino etc.), (16) di-$C_{1-6}$ alkylamino (e.g., dimethylamino, diethylamino etc.), (17) di-$C_{6-14}$ arylamino (e.g., diphenylamino etc.), (18) di-$C_{7-16}$ aralkylamino (e.g., dibenzylamino etc.), (19) formyl, (20) $C_{1-6}$ alkyl-carbonyl (e.g., acetyl, propionyl etc.), (21) $C_{6-14}$ aryl-carbonyl (e.g., benzoyl, 1-naphthoyl, 2-naphthoyl etc.), (22) carboxyl, (23) $C_{1-6}$ alkoxy-carbonyl (e.g., methoxycarbonyl, ethoxycarbonyl, propoxycarbonyl, tert-butoxycarbonyl etc.), (24) $C_{6-14}$ aryloxy-carbonyl (e.g., phenoxycarbonyl etc.), (25) carbamoyl, (26) thiocarbamoyl, (27) mono-$C_{1-6}$ alkyl-carbamoyl (e.g., methylcarbamoyl, ethylcarbamoyl etc.), (28) di-$C_{1-6}$ alkyl-carbamoyl (e.g., dimethylcarbamoyl, diethylcarbamoyl, ethylmethylcarbamoyl etc.), (29) $C_{6-14}$ aryl-carbamoyl (e.g., phenyl carbamoyl, 1-naphthylcarbamoyl, 2-naphthylcarbamoyl etc.), (30) $C_{1-6}$ alkylsulfonyl (e.g., methylsulfonyl, ethylsulfonyl etc.), (31) $C_{6-14}$ arylsulfonyl (e.g., phenylsulfonyl, 1-naphthylsulfonyl, 2-naphthylsulfonyl etc.), (32) $C_{1-6}$ alkylsulfinyl (e.g., methylsulfinyl, ethylsulfinyl etc.), (33) $C_{6-14}$ arylsulfinyl (e.g., phenylsulfinyl, 1-naphthylsulfinyl, 2-naphthylsulfinyl etc.), (34) formylamino, (35) $C_{1-6}$ alkyl-carbonylamino (e.g., acetylamino etc.), (36) $C_{6-14}$ aryl-carbonylamino (e.g., benzoylamino, naphthoylamino etc.), (37) $C_{1-6}$ alkoxy-carbonylamino (e.g., methoxycarbonylamino, ethoxycarbonylamino, propoxycarbonylamino, butoxycarbonylamino etc.), (38) $C_{1-6}$ alkylsulfonylamino (e.g., methylsulfonylamino, ethylsulfonylamino etc.), (39) $C_{6-14}$ arylsulfonylamino (e.g., phenylsulfonylamino, 2-naphthylsulfonylamino, 1-naphthylsulfonylamino etc.) (40) $C_{1-6}$ alkyl-carbonyloxy (e.g., acetoxy, propionyloxy etc.), (41) $C_{6-14}$ aryl-carbonyloxy (e.g., benzoyloxy, naphthylcarbonyloxy etc.), (42) $C_{1-6}$ alkoxy-carbonyloxy (e.g., methoxycarbonyloxy, ethoxycarbonyloxy, propoxycarbonyloxy, butoxycarbonyloxy etc.), (43) mono-$C_{1-6}$ alkyl-carbamoyloxy (e.g., methylcarbamoyloxy, ethylcarbamoyloxy etc.), (44) di-$C_{1-6}$ alkyl-carbamoyloxy (e.g., dimethylcarbamoyloxy, diethylcarbamoyloxy etc.), (45) $C_{6-14}$ aryl-carbamoyloxy (e.g., phenylcarbamoyloxy, naphthylcarbamoyloxy etc.), (46) 5- to 7-membered saturated cyclic amino optionally containing, besides one nitrogen atom and a carbon atom, one or two kinds of 1 to 4 hetero atoms selected from a nitrogen atom, a sulfur atom and an oxygen atom (e.g., pyrrolidin-1-yl, piperidino, piperazin-1-yl, morpholino, thiomorpholino, hexahydroazepin-1-yl etc.), (47) a 5- to 10-membered aromatic heterocyclic group containing, besides a carbon atom, one or two kinds of 1 to 4 hetero atoms selected from a nitrogen atom, a sulfur atom and an oxygen atom (e.g., 2-thienyl, 3-thienyl, 2-pyridyl, 3-pyridyl, 4-pyridyl, 2-quinolyl, 3-quinolyl, 4-quinolyl, 5-quinolyl, 8-quinolyl, 1-isoquinolyl, 3-isoquinolyl, 4-isoquinolyl, 5-isoquinolyl, 1-indolyl, 2-indolyl, 3-indolyl, 2-benzothiazolyl, 2-benzo[b]thienyl, 3-benzo[b]thienyl, 2-benzo[b]furanyl, 3-benzo[b] furanyl etc.), (48) $C_{1-3}$ alkyl enedioxy (e.g., methylenedioxy, ethylenedioxy etc.), (49) $C_{3-7}$ cycloalkyl (e.g., cyclopropyl, cyclobutyl, cyclopentyl, cyclohexyl, cycloheptyl etc.) and the like.

The number of the substituents is 1 to 3.

Examples of the "acyl group" for $R^3$ or $R^4$ include an acyl group having 1-20 carbon atoms and derived from organic carboxylic acid. For example, a $C_{1-7}$ alkanoyl group (e.g., formyl; $C_{1-6}$ alkyl-carbonyl such as acetyl, propionyl, butyryl, isobutyryl, pentanoyl, hexanoyl, heptanoyl and the like etc.), a $C_{6-14}$ aryl-carbonyl group (e.g., benzoyl, naphthalenecarbonyl etc.), a $C_{1-6}$ alkoxy-carbonyl group (e.g., methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl etc.), a $C_{1-4}$ aryloxy-carbonyl group (e.g., phenoxycarbonyl group), a $C_{7-19}$ aralkyl-carbonyl group (e.g., phenyl-$C_{1-4}$ alkylcarbonyl such as benzylcarbonyl, phenethylcarbonyl, phenylpropylcarbonyl and the like, naphthyl-$C_{1-4}$ alkylcarbonyl such as benzhydrylcarbonyl, naphthylethylcarbonyl and the like, etc.), a $C_{7-19}$ aralkyloxy-carbonyl group (e.g., phenyl-$C_{1-4}$ alkyloxycarbonyl such as benzyloxycarbonyl and the like etc.), a 5- or 6-membered heterocyclylcarbonyl group or a fused heterocyclylcarbonyl group thereof (e.g., 5- or 6-membered heterocyclyl-carbonyl group containing 1 to 4 hetero atoms such as nitrogen atom (optionally oxidized), oxygen atom, sulfur atom (optionally mono- or di-oxidized) such as pyrrolylcarbonyl such as 2- or 3-pyrrolylcarbonyl and the like; pyrazolylcarbonyl such as 3-, 4- or 5-pyrazolylcarbonyl and the like; imidazolylcarbonyl such as 2-, 4- or 5-imidazolylcarbonyl and the like; triazolylcarbonyl such as 1,2,3-triazol-4-ylcarbonyl, 1,2,4-triazol-3-ylcarbonyl and the like; tetrazolyl carbonyl such as 1H- or 2H-tetrazol-5-ylcarbonyl and the like; furylcarbonyl such as 2- or 3-furylcarbonyl and the like; thienylcarbonyl such as 2- or 3-thienylcarbonyl and the like; oxazolylcarbonyl such as 2-, 4- or 5-oxazolylcarbonyl and the like; isoxazolylcarbonyl such as 3-, 4- or 5-isoxazolylcarbonyl and the like;

oxadiazolylcarbonyl such as 1,2,3-oxadiazol-4- or 5-ylcarbonyl, 1,2,4-oxadiazol-3- or 5-ylcarbonyl, 1,2,5-oxadiazol-3- or 4-ylcarbonyl, 1,3,4-oxadiazol-2-ylcarbonyl and the like; thiazolylcarbonyl such as 2-, 4- or 5-thiazolylcarbonyl and the like; isothiazolylcarbonyl such as 3-, 4- or 5-isothiazolylcarbonyl and the like; thiadiazolylcarbonyl such as 1,2,3-thiadiazol-4- or 5-ylcarbonyl, 1,2,4-thiadiazol-3- or 5-ylcarbonyl, 1,2,5-thiadiazol-3- or 4-ylcarbonyl, 1,3,4-thiadiazol-2-ylcarbonyl and the like; pyrrolidinylcarbonyl such as 2- or 3-pyrrolidinylcarbonyl and the like; pyridylcarbonyl such as 2-, 3- or 4-pyridylcarbonyl and the like; pyridylcarbonyl such as 2-, 3- or 4-pyridyl-N-oxidocarbonyl and the like, wherein a nitrogen atom is oxidized; pyridazinylcarbonyl such as 3- or 4-pyridazinylcarbonyl and the like; pyridazinylcarbonyl such as 3-, 4-, 5- or 6-pyridazinyl-N-oxidocarbonyl and the like, wherein one or both of the nitrogen atoms is/are oxidized; pyrimidinylcarbonyl such as 2-, 4- or 5-pyrimidinylcarbonyl and the like; pyrimidinylcarbonyl such as 2-, 4-, 5- or 6-pyrimidinyl-N-oxidocarbonyl and the like, wherein one or both of the nitrogen atoms is/are oxidized; pyrazinylcarbonyl; piperidinylcarbonyl such as 2-, 3- or 4-piperidinylcarbonyl and the like; piperazinylcarbonyl; indolylcarbonyl such as 3H-indol-2- or 3-ylcarbonyl and the like; pyranylcarbonyl such as 2-, 3- or 4-pyranylcarbonyl and the like; thiopyranylcarbonyl such as 2-, 3- or 4-thiopyranylcarbonyl and the like; quinolylcarbonyl such as 3-, 4-, 5-, 6-, 7- or 8-quinolylcarbonyl and the like; isoquinolylcarbonyl; pyrido[2,3-d]pyrimidinylcarbonyl (e.g., pyrido[2,3-d]pyrimidin-2-ylcarbonyl); naphthyridinylcarbonyl such as 1,5-, 1,6-, 1,7-, 1,8-, 2,6- or 2,7-naphthyridinylcarbonyl and the like (e.g., 1,5-naphthyridin-2- or 3-ylcarbonyl); thieno[2,3-d]pyridylcarbonyl (e.g., thieno[2,3-d]pyridin-3-ylcarbonyl); pyrazinoquinolylcarbonyl (e.g., pyrazino[2,3-b]quinolin-2-ylcarbonyl); chromenylcarbonyl (e.g., 2H-chromen-2- or 3-ylcarbonyl etc.) and the like, a 5- or 6-membered heterocyclyl-acetyl group (e.g., 5- or 6-membered heterocyclyl-acetyl group containing 1 to 4 hetero atoms such as nitrogen atom (optionally oxidized), oxygen atom, sulfur atom, (optionally mono- or di-oxidized) and the like (e.g., 2-pyrrolylacetyl, 3-imidazolylacetyl, 5-isooxazolylacetyl and the like), and the like are used.

Regarding the substituent of the acyl group, for example, when the above-mentioned acyl group is an alkanoyl group or an alkoxy-carbonyl group, the acyl group may be substituted by 1 to 3 alkylthio groups (e.g., $C_{1-4}$ alkylthio such as methylthio, ethylthio, n-propylthio, isopropylthio and the like, and the like), halogen (e.g., fluorine, chlorine, bromine, iodine), an alkoxy group (e.g., $C_{1-6}$ alkoxy such as methoxy, ethoxy, n-propoxy, tert-butoxy, n-hexyloxy and the like, and the like), a nitro group, an alkoxy-carbonyl group (e.g., $C_{1-6}$ alkoxy-carbonyl such as methoxycarbonyl, ethoxycarbonyl, n-propoxycarbonyl, isopropoxycarbonyl, n-butoxycarbonyl, isobutoxycarbonyl, sec-butoxycarbonyl, tert-butoxycarbonyl and the like, and the like), an alkylamino group (e.g., mono- or di-$C_{1-6}$ alkylamino such as methylamino, ethylamino, n-propylamine, n-butylamino, tert-butylamino, n-pentylamino, n-hexylamino, dimethylamino, di ethylamino, methyl ethyl amino, di-(n-propyl)amino, di-(n-butyl) amino and the like, and the like), an alkoxyimino group (e.g., $C_{1-6}$ alkoxyimino such as methoxyimino, ethoxyimino, n-propoxyimino, tert-butoxyimino, n-hexyloxy-imino and the like, and the like) or hydroxyimino.

When the above-mentioned acyl group is an aryl-carbonyl group, an aryloxy-carbonyl group, an aralkyl-carbonyl group, an aralkyloxycarbonyl group, a 5- or 6-membered heterocyclyl-carbonyl group, or a 5- or 6-membered heterocyclyl-acetyl group, it may be substituted by 1-5 (preferably 1-3) alkyl groups (e.g., $C_{1-6}$ alkyl such as methyl, ethyl, n-propyl, isopropyl, n-butyl, isobutyl, sec-butyl, tert-butyl, n-pentyl, sec-pentyl, isopentyl, neopentyl, n-hexyl, isohexyl and the like, $C_{3-6}$ cycloalkyl such as cyclohexyl and the like, and the like), an alkenyl group (e.g., $C_{2-6}$ alkenyl such as allyl, isopropenyl, isobutenyl, 1-methylallyl, 2-pentenyl, 2-hexenyl and the like, and the like), an alkynyl group (e.g., $C_{2-6}$ alkynyl such as propargyl, 2-butynyl, 3-butynyl, 3-pentynyl, 3-hexynyl and the like, and the like), an alkoxy group (e.g., $C_{1-6}$ alkoxy such as methoxy, ethoxy, n-propoxy, tert-butoxy, n-hexyloxy and the like, and the like), an acyl group [e.g., $C_{1-7}$ alkanoyl such as formyl, acetyl, propionyl, butyryl, isobutyryl, pentanoyl, hexanoyl, heptanoyl and the like; $C_{6-14}$ aryl-carbonyl such as benzoyl, naphthalenecarbonyl and the like; $C_{1-6}$ alkoxy-carbonyl such as methoxycarbonyl, ethoxycarbonyl, propoxycarbonyl, isopropoxycarbonyl, butoxycarbonyl, isobutoxycarbonyl, sec-butoxycarbonyl, tert-butoxycarbonyl and the like; $C_{6-14}$ aryloxy-carbonyl such as phenoxycarbonyl and the like; $C_{7-19}$ aralkyl-carbonyl such as phenyl-$C_{1-4}$ alkyl-carbonyl (e.g., benzylcarbonyl, phenethylcarbonyl, phenylpropylcarbonyl and the like) and the like; $C_{7-19}$ aralkyloxy-carbonyl such as phenyl-$C_{1-4}$ alkyloxy-carbonyl (e.g., benzyloxycarbonyl and the like) and the like, and the like), nitro, amino, hydroxy, cyano, sulfamoyl, mercapto, halogen (e.g., fluorine, chlorine, bromine, iodine), or an alkylthio group ($C_{1-4}$ alkylthio such as methylthio, ethylthio, n-propylthio, isobutylthio and the like, and the like).

Examples of the "optionally substituted hydroxy group" for $R^3$ or $R^4$ include hydroxy; $C_{1-6}$ alkoxy optionally having 1 to 3 halogen atoms (e.g., fluorine, chlorine, bromine, iodine) (e.g., methoxy, ethoxy, propoxy, isopropoxy, butoxy, isobutoxy, sec-butoxy, pentyloxy, hexyloxy, trifluoromethoxy etc.); $C_{6-14}$ aryloxy (e.g., phenyl oxy, naphthyloxy etc.), $C_{7-16}$ aralkyloxy (e.g., benzyloxy, phenethyloxy, diphenylmethyloxy, 1-naphthylmethyloxy, 2-naphthylmethyloxy, 2,2-diphenylethyloxy, 3-phenylpropyloxy, 4-phenylbutyloxy, 5-phenylpentyloxy etc.); $C_{1-6}$ alkyl-carbonyloxy (e.g., acetoxy, propionyloxy etc.); $C_{5-14}$ aryl-carbonyloxy (e.g., benzoyloxy, naphthylcarbonyloxy etc.); $C_{1-6}$ alkoxy-carbonyloxy (e.g., methoxycarbonyloxy, ethoxycarbonyloxy, propoxycarbonyloxy, butoxycarbonyloxy etc.); mono-$C_{1-6}$ alkyl-carbamoyloxy (e.g., methylcarbamoyloxy, ethylcarbamoyloxy etc.); di-$C_{1-6}$ alkyl-carbamoyloxy (e.g., dimethylcarbamoyloxy, diethylcarbamoyloxy etc.); $C_{6-14}$ aryl-carbamoyloxy (e.g., phenylcarbamoyloxy, naphthylcarbamoyloxy etc.) and the like.

Examples of the "optionally substituted amino group" for $R^3$ or $R^4$ include amino; mono-$C_{1-6}$ alkylamino (e.g., methylamino, ethylamino etc.); mono-$C_{6-14}$ arylamino (e.g., phenylamino, 1-naphthylamino, 2-naphthylamino etc.); mono-$C_{7-16}$ aralkylamino (e.g., benzylamino etc.); di-$C_{1-6}$ alkylamino (e.g., dimethylamino, diethylamino etc.); $d_{6-14}$ arylamino (e.g., diphenylamino etc.); di-$C_{7-16}$ aralkylamino (e.g., dibenzylamino etc.); formylamino; $C_{1-6}$ alkyl-carbonylamino (e.g., acetylamino etc.); $C_{6-14}$ aryl-carbonylamino (e.g., benzoylamino, naphthoylamino etc.); $C_{1-6}$ alkoxy-carbonylamino (e.g., methoxycarbonylamino, ethoxycarbonylamino, propoxycarbonylamino, tert-butoxycarbonylamino etc.); $C_{7-16}$ aralkyloxycarbonylamino (e.g., benzyloxycarbonylamino etc.); $C_{1-6}$ alkylsulfonylamino (e.g., methylsulfonylamino, ethylsulfonylamino etc.); $C_{6-14}$ arylsulfonylamino (e.g., phenylsulfonylamino, 2-naphthylsulfonylamino, 1-naphthylsulfonylamino etc.) and the like.

Examples of the "alkyl group" for $R^5$ include $C_{1-4}$ alkyl groups such as methyl, ethyl, propyl, isopropyl, butyl, isobutyl, sec-butyl, tert-butyl and the like, and the like.

Preferred as $R^1$ is a pyridin-3-yl group optionally substituted by 1 to 3 substituents selected from (i) halogen (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) an amino group optionally substituted by $C_{1-6}$ alkyl (e.g., methyl, ethyl, propyl, isopropyl, butyl, isobutyl, sec-butyl, tert-butyl, pentyl, hexyl etc.) and (vi) $C_{1-6}$ alkoxy-carbonyl (e.g., methoxycarbonyl, ethoxycarbonyl, propoxycarbonyl, tert-butoxycarbonyl etc.).

More preferred as $R^1$ is a pyridin-3-yl group optionally substituted by 1 to 3 substituents selected from (i) halogen (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine) and (v) an amino group optionally substituted by $C_{1-6}$ alkyl (e.g., methyl, ethyl, propyl, isopropyl, butyl, isobutyl, sec-butyl, tert-butyl, pentyl, hexyl etc.). Further preferred is a pyridin-3-yl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine). Particularly preferred as $R^1$ is a pyridin-3-yl group.

Preferred as $R^2$ is [1] a $C_{6-14}$ aryl group (e.g., phenyl group) optionally substituted by 1-5 (preferably 1-3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) $C_{1-6}$ alkylthio (e.g., methylthio, ethylthio, propylthio, isopropylthio, butylthio, isobutylthio, sec-butylthio, pentylthio, hexylthio etc.) optionally substituted by 1-5 (preferably 1-3) halogens (e.g., fluorine, chlorine, bromine, iodine) and (ix) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine) and (v) acetyl, and

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) acyl (e.g., acetyl) and (vi) nitro.

Of these, preferred as $R^2$ is [1] a $C_{6-14}$ aryl group (e.g., phenyl group) optionally substituted by 1-5 (preferably 1-3) substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine) and (v) acetyl,

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) acyl (e.g., acetyl) and (vi) nitro.

Particularly preferred is [1] a phenyl group optionally substituted by 1-5 (preferably 1-3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine),

[2] a thienyl group optionally substituted by 1 to 3 substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine).

Among those mentioned above, a preferable embodiment of $R^2$ is [1] a phenyl group optionally substituted by 1 to 5 substituents selected from (i) a halogen atom and (ii) $C_{1-6}$ alkyl optionally substituted by 1-5 halogen atoms, or [2] a pyridyl group optionally substituted by 1 to 4 substituents selected from lower ($C_{1-6}$) alkyl, a halogen atom, alkoxy ($C_{1-6}$ alkoxy), cyano, acyl (e.g., acetyl) and nitro and the like.

Particularly preferred as $R^2$ is a phenyl group, a 2-fluorophenyl group, a 2-methylphenyl group, a 2-fluoropyridin-3-yl group, a 3-fluoropyridin-4-yl group, a 2-chloropyridin-3-yl group, a 6-chloropyridin-3-yl group, a 4-methylpyridin-3-yl group, a 2-methylpyridin-3-yl group, a 3-methylpyridin-2-yl group, a 2-trifluoromethylpyridin-3-yl group, or a 6'-chloro-2,3'-bipyridin-5-yl group.

Preferably, $R^3$ and $R^4$ are each independently a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom, and particularly preferred is a hydrogen atom.

Preferred as $R^5$ is methyl or ethyl, and particularly preferred is methyl.

A preferable embodiment of the above-mentioned substituents for $R^1$-$R^5$ is any combination thereof.

In a preferable embodiment, for example, $R^1$ is a pyridin-3-yl group optionally substituted by 1 to 3 substituents selected from (i) halogen (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) an amino group optionally substituted by $C_{1-6}$ alkyl (e.g., methyl, ethyl, propyl, isopropyl, butyl, isobutyl, sec-butyl, tert-butyl, pentyl, hexyl etc.) and (vi) $C_{1-6}$ alkoxy-carbonyl (e.g., methoxycarbonyl, ethoxycarbonyl, propoxycarbonyl, tert-butoxycarbonyl etc.);

$R^2$ is [1] a $C_{6-14}$ aryl group (e.g., phenyl group) optionally substituted by 1-5 (preferably 1-3) substituents selected from, (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) acetyl, (vi) $C_{3-7}$ cycloalkyl (e.g., cyclopropyl, cyclobutyl, cyclopentyl, cyclohexyl, cycloheptyl etc.), (vii) $C_{1-6}$ alkylsulfonyl (e.g., methylsulfonyl, ethylsulfonyl etc.), (viii) $C_{1-6}$ alkylthio (e.g., methylthio, ethylthio, propylthio, isopropylthio, butylthio, isobutylthio, sec-butylthio, pentylthio, hexylthio etc.) optionally substituted by 1-5 (preferably 1-3) halogens (e.g., fluorine, chlorine, bromine, iodine) and (ix) $C_{1-6}$ alkylsulfinyl (e.g., methylsulfinyl, ethylsulfinyl etc.),

[2] a thienyl group optionally substituted by 1 to 3 substituents selected from (i) a halogen atom (e.g., fluorine, chlorine, bromine, iodine), (ii) cyano, (iii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine) and (v) acetyl, or

[3] a pyridyl group optionally substituted by 1 to 4 substituents selected from (i) a halogen atom (e.g., fluorine, chlorine, bromine, iodine), (ii) cyano, (iii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), (iv) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), (v) acyl (e.g., acetyl) and (vi) nitro;

$R^3$ and $R^4$ are each independently a hydrogen atom, a $C_{1-6}$ alkyl group (e.g., methyl, ethyl, n-propyl, isobutyl etc.), a $C_{1-6}$ alkyl-carbonyl group (e.g., acetyl, propionyl, butyryl, isobutyryl, pentanoyl, hexanoyl, heptanoyl etc.), a fluorine atom or a chlorine atom; and $R^5$ is methyl or ethyl.

In a particularly preferable embodiment, $R^1$ is a pyridin-3-yl group optionally substituted by 1 to 3 substituents selected from (i) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine) and (ii) $C_{1-6}$ alkoxy (e.g., methoxy, ethoxy, propoxy, isopropoxy, butoxy, isobutoxy, sec-butoxy, pentyloxy, hexyloxy etc.) optionally substituted by 1-5 (preferably 1-3) halogens (e.g., fluorine, chlorine, bromine, iodine), $R^2$ is [1] a phenyl group optionally substituted by 1-5 (preferably 1-3) substituents selected from (i) a halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine),

[2] a thienyl group optionally substituted by 1 to 3 substituents selected from (i) halogen atom (e.g., fluorine, chlorine, bromine, iodine) and (ii) $C_{1-6}$ alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), or

[3] a pyridyl group optionally substituted by 1 to 4 substituents selected from (i) a halogen atom (e.g., fluorine, chlorine, bromine, iodine) and (ii) lower (specifically $C_{1-6}$) alkyl (e.g., methyl, ethyl, propyl, isopropyl, butyl, isobutyl, sec-butyl, tert-butyl, pentyl, hexyl etc.) optionally substituted by 1-5 (preferably 1-3) halogens (e.g., fluorine, chlorine, bromine, iodine), $R^3$ and $R^4$ is a hydrogen atom, and $R^5$ is methyl.

Of these, in a particularly preferable embodiment, $R^1$ is a pyridin-3-yl group, $R^2$ is a phenyl group optionally substituted by 1-5 (preferably 1-3) halogen atoms (e.g., fluorine, chlorine, bromine, iodine), $R^3$ and $R^4$ are hydrogen atoms, and $R^5$ is methyl.

Preferable examples of the object compound (VI) include 1-{5-(2-fluorophenyl)-1-[(6-methylpyridin-3-yl) sulfonyl]-1H-pyrrol-3-yl}-N-methylmethanamine or a salt thereof, 1-[4-fluoro-5-phenyl-1-(pyridin-3-ylsulfonyl)-1H-pyrrol-3-yl]-N-methylmethanamine or a salt thereof, N-methyl-1-[5-(4-methyl-3-thienyl)-1-(pyridin-3-ylsulfonyl)-1H-pyrrol-3-yl]methanamine or a salt thereof, 1-[5-(2-fluoropyridin-3-yl)-1-(pyridin-3-ylsulfonyl)-1H-pyrrol-3-yl]-N-methylmethanamine or a salt thereof, 1-[5-(2-fluorophenyl)-1-(pyridin-3-ylsulfonyl)-1H-pyrrol-3-yl]-N-methylmethanamine or a salt thereof, N-methyl-1-[5-(2-methylphenyl)-1-(pyridin-3-ylsulfonyl)-1H-pyrrol-3-yl] methanamine or a salt thereof and the like.

The production method, of the present invention is explained in detail below.

Examples of the salt of compounds (I)-(VI) in the reaction formulas include a metal salt, an ammonium salt, a salt with an organic base, a salt with an inorganic acid, a salt with an organic acid, a salt with basic or acidic amino acid, etc. Suitable examples of the metal salt include an alkali metal salt such as a sodium salt, a potassium salt, etc.; an alkaline earth metal salt such as a calcium salt, a magnesium salt, a barium, salt, etc.; an aluminum salt, etc. Suitable examples of the salts with an organic base include salts with trimethylamine, triethylamine, pyridine, picoline, 2,6-lutidine, ethanolamine, diethanolamine, triethanolamine, cyclohexylamine, dicyclohexylamine, N,N'-dibenzylethylenediamine, etc. Suitable examples of the salts with an inorganic acid include salts with hydrochloric acid, hydrobromic acid, nitric acid, sulfuric acid, phosphoric acid, etc. Suitable examples of the salts with an organic acid include salts with formic acid, acetic acid, trifluoroacetic acid, phthalic acid, fumaric acid, oxalic acid, tartaric acid, maleic acid, citric acid, succinic acid, malic acid, methanesulfonic acid, benzenesulfonic acid, p-toluenesulfonic acid, etc. Suitable examples of the salts with basic amino acid include salts with arginine, lysine, ornithine, etc. Suitable examples of the salts with acidic amino acid include salts with aspartic acid and glutamic acid, etc.

The compound, obtained, in each step can be used after obtained in the form of a reaction mixture or a crude product for the next reaction. In addition, it can be isolated from a reaction mixture by a conventional method, and easily purified by conventional separation means such as recrystallization, distillation, chromatography and the like.

(Production Method 1)

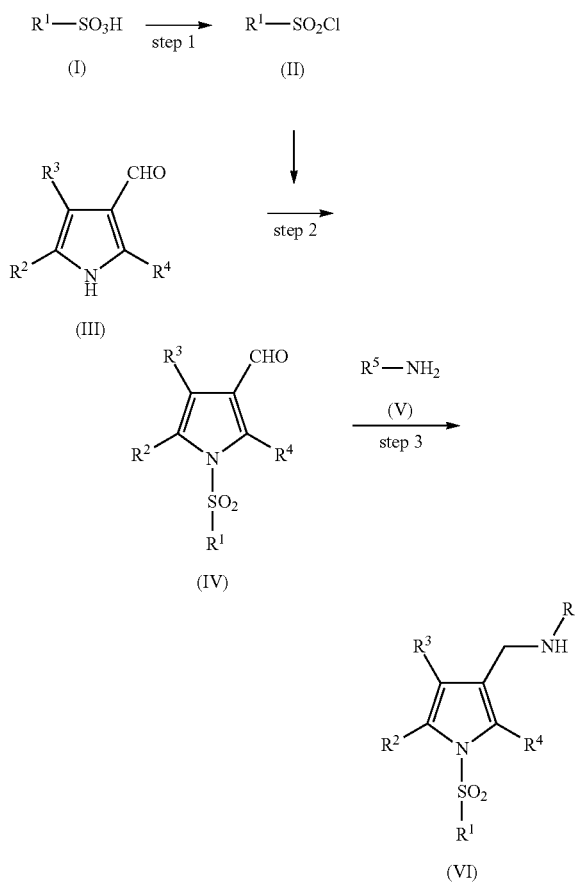

wherein each symbol is as defined above.
(Step 1)
A pyridine-3-sulfonyl chloride compound (to be also referred to as compound (II)) can be produced by reacting a pyridine-3-sulfonic acid compound (hereinafter to be also referred to as compound (I)) with phosphorus pentachloride in a solvent of chlorobenzene or trifluoromethylbenzene.

The amount of phosphorus pentachloride to be used is generally 1-10 equivalents, preferably 1-5 equivalents, more preferably 1-3 equivalents, relative to compound (I).

The amount of chlorobenzene or trifluoromethylbenzene to be used is generally 1-100 mL, preferably 1-50 mL, per 1 g of compound (I).

The reaction temperature is generally 50-150° C., preferably 100-150° C.

The reaction time is generally 1-24 hr, preferably 1-10 hr.
(Step 2)
Compound (IV) can be produced by reacting, without isolation, compound (II) obtained in step 1 with compound (III) or a salt thereof.

The amount of compound (II) to be used is preferably about 1-about 10 mol, more preferably about 1-about 5 mol, per 1 mol of compound (III).

This reaction is advantageously performed in an inert solvent. While such solvent is not particularly limited as long as the reaction proceeds, examples thereof include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), nitriles (e.g., acetonitrile, propionitrile and the like), water and a mixture thereof. The amount of the solvent to be used is generally 1-100 mL, preferably 1-50 mL, per 1 g of compound (III).

This reaction is preferably performed in the presence of a base. Examples of the base include inorganic bases such as sodium hydride, sodium hydroxide, potassium hydroxide and the like, basic salts such as sodium carbonate, potassium, carbonate, cesium carbonate, sodium hydrogen carbonate and the like, metal bases such as potassium ethoxide, potassium tert-butoxide, sodium methoxide, sodium ethoxide and the like, aromatic amines such as pyridine, lutidine and the like, tertiary amines such as diisopropylethylamine, triethylamine, tripropylamine, tributylamine, cyclohexyldimethylamine, 4-N,N-dimethylaminopyridine, N,N-dimethylaniline, N-methylpiperidine, N-methylpyrrolidine, N-methylmorpholine and the like, or a mixture of these and the like. The amount of the base to be used is generally about 0.01-about 10 mol, preferably about 0.1-about 5 mol, per 1 mol of compound (III).

In addition, this reaction can also be performed in the co-presence of crown ether. Examples of crown ether include 15-crown-5-ether, 18-crown-6-ether and the like. The amount of crown ether to be used is generally about 1-about 10 mol, preferably about 1-about 5 mol, per 1 mol of compound (III).

The reaction time is generally about 30 min-about 24 hr, preferably about 30 min-about 8 hr. The reaction temperature is generally about 0° C.-about 100° C., preferably about 10° C. -about 50° C.
(Step 3)
Compound (VI) or a salt thereof can be produced by reacting compound (IV) or a salt thereof with compound (V) or a salt thereof and reducing the formed imine. Alternatively, compound (VI) or a salt thereof can be obtained by reacting compound (IV) or a salt thereof with compound (V) or a salt thereof in the presence of a reducing agent and without isolating the formed imine.

This reaction can be performed according to the reaction conditions conventionally known as the reductive amination reaction. For example, it can be performed according to the method described in Shinjikken Kagaku Koza (Courses in Experimental Chemistry), vol. 14-III, pages 1380-1385 (Maruzen).

The amount of compound (V) to be used is preferably about 1-about 10 mol, more preferably about 1-about 5 mol, per 1 mol of compound (IV).

This reaction is advantageously performed in a solvent inert to the reaction. While such solvent is not particularly limited as long as the reaction proceeds, examples thereof include alcohols (e.g., methanol, ethanol, propanol, butanol and the like), aromatic hydrocarbons (e.g., benzene, toluene, xylene, chlorobenzene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water, and a mixture thereof. The amount of the solvent to be used is generally 1-100 mL, preferably 1-50 mL, per 1 g of compound (IV).

The reaction time is generally about 0.5-about 24 hr, preferably about 0.5-about 10 hr. The reaction, temperature is generally about −50° C.-about 100° C., preferably about −10° C. -about 50° C.

As the reducing agent, sodium borohydride, sodium cyanoborohydride, sodium triacetoxyborohydride and the like can be used. The amount of the reducing agent to be used is preferably about 0.2-about 10 mol, more preferably about 0.2-about 5 mol, per 1 mol of compound (IV).

The reduction can also be performed by catalytic hydrogenation.

The catalytic hydrogenation can be performed in the presence of a hydrogen source and a metal catalyst. Examples of the metal catalyst include palladium catalysts (e.g., palladium carbon, palladium hydroxide carbon, palladium oxide and the like), nickel catalysts (e.g., Raney-nickel and the like), platinum catalysts (e.g., platinum oxide, platinum carbon and the like), rhodium catalyst (e.g., rhodium carbon and the like), cobalt catalysts (e.g., Raney cobalt and the like) and the like. Among these, palladium carbon or Raney-nickel is preferable. The amount of the metal catalyst to be used is generally about 0.01-about 10 mol, preferably about 0.01-about 5 mol, per 1 mol of compound (IV).

Examples of the hydrogen source include hydrogen gas, formic acid, ammonium formate, triethylammonium formate, sodium phosphinate, hydrazine and the like. When a hydrogen source other than the hydrogen gas is used, a compound, of the hydrogen source is generally used in about 1-about 100 mol, preferably about 1-about 50 mol, more preferably about 1-about 10 mol, for example, about 1-about 5 mol, per 1 g of compound (IV).

The reduction is advantageously performed in a solvent inert to the reaction. While such solvent is not particularly limited as long as the reaction proceeds, examples thereof include alcohols (e.g., methanol, ethanol, propanol, butanol and the like), hydrocarbons (e.g., benzene, toluene, xylene and the like), halogenated hydrocarbons (e.g., dichloromethane, chloroform and the like), ethers (e.g., diethyl ether, dioxane, tetrahydrofuran and the like), esters (e.g., ethyl acetate and the like), amides (e.g., N,N-dimethylformamide, N,N-dimethylacetamide and the like), water and a mixture thereof. The amount of the solvent to be used is generally 1-100 mL, preferably 1-50 mL, per 1 g of compound (IV).

The reaction time is generally about 0.5-about 24 hr, preferably about 0.5-about 10 hr. The reaction temperature is generally about −50° C.-about 100° C., preferably about −20° C.-about 50° C.

Compound (VI) obtained by the method of the present invention has a proton pump inhibitory action, and effectively suppresses secretion of gastric acid. In addition, it has low toxicity (e.g., acute toxicity, chronic toxicity, genetic toxicity, reproductive toxicity, cardiac toxicity, drug interaction, carcinogenicity, etc.) and high water-solubility, and is excellent in the aspects of stability, pharmacokinetics (absorption, distribution, metabolism, excretion, etc.) and efficacy, thus being useful as medicine.

Compound (VI) obtained by the method of the present invention is useful for mammals (e.g., human, monkey, sheep, bovine, horse, dog, cat, rabbit, rat, mouse etc.) in the treatment or prophylaxis of peptic ulcer (e.g., gastric ulcer, gastric ulcer due to postoperative stress, duodenal ulcer, anastomotic ulcer, ulcer caused by non-steroidal anti-inflammatory agent etc.); Zollinger-Ellison syndrome; gastritis; erosive esophagitis; reflux esophagitis such as erosive reflux esophagitis and the like; symptomatic, gastroesophageal reflux disease (symptomatic GERD) such as non-erosive gastroesophageal, reflux disease, gastroesophageal reflux disease free of esophagitis and the like; functional dyspepsia; gastric cancer (including gastric cancer associated with promoted production of interleukin-1β by gene polymorphism of interleukin-1); gastric MALT lymphoma; hyperacidity; peptic ulcer, acute stress ulcer, hemorrhagic gastritis or upper gastrointestinal hemorrhage due to invasive stress (e.g., stress produced by major surgery requiring postsurgery intensive management and cerebrovascular diseases, head trauma, multiple organ disorder, extensive burn requiring intensive treatment) and the like; airway disorders; asthma and the like, pre-anesthetic administration, eradication or eradication assistance of *Helicobacter pylori*, and the like.

As used herein, the above-mentioned reflux esophagitis and symptomatic gastroesophageal reflux disease (symptomatic GERD) are sometimes combinedly referred to simply as GERD.

The content of compound (VI) obtained by the method of the present invention in a pharmaceutical composition containing the compound is about 0.01 to 100 wt % of the whole composition. While the dose varies depending on the subject of administration, administration route, disease and the like, it is, for example, about 0.5-about 1500 mg/day, preferably about 5-about 150 mg/day, of the active ingredient when orally administered as an anti-ulcer agent to an adult (60 kg). Compound (VI) obtained by the method of the present invention may be administered once per day or in 2-3 portions per day.

Compound (VI) obtained by the method of the present invention has low toxicity, and can be safely administered as it is or as a pharmaceutical composition mixed with a pharmacologically acceptable carrier according to a method known per se, for example, a tablet (including a sugar-coated tablet and a film-coated tablet), a powder, a granule, a capsule (including soft capsule), an orally disintegrating tablet, an orally disintegrable film, a liquid, an injectable preparation, a suppository, a sustained release preparation, a patch and the like, orally or parenterally (e.g., topical, rectal, intravenous administration etc.). Particularly, it is preferably administered as an oral preparation such as tablet, granule, capsule and the like.

A pharmacologically acceptable carrier usable for the production of the pharmaceutical composition of the present invention may be exemplified by various organic or inorganic carrier materials that are conventionally used as preparation materials. Examples thereof include excipient, lubricant, binding agent, disintegrant, water-soluble polymer and basic inorganic salt for solid preparations; solvent, solubilizing agent, suspending agent, isotonic agent, buffering agent, soothing agent and the like for liquid preparations. Conventional additives such as preservative, antioxidant, colorant, sweetening agent, souring agent, bubbling agent, flavor and the like can also be used as necessary.

Examples of the "excipient" include lactose, white sugar, D-mannitol, starch, corn starch, crystalline cellulose, light anhydrous silicic acid, titanium oxide and the like.

Examples of the "lubricant" include magnesium stearate, sucrose ester of fatty acid, polyethylene glycol, talc, stearic acid and the like.

Examples of the "binding agent" include hydroxypropylcellulose, hydroxypropylmethylcellulose, crystalline cellulose, starch, polyvinylpyrrolidone, gum arabic powder, gelatin, pullulan, low-substituted hydroxypropylcellulose and the like.

Examples of the "disintegrant" include (1) crospovidone, (2) disintegrant called super-disintegrant such as croscarmellose sodium (FMC-Asahi Kasei Corporation), carmellose calcium (GOTOKU CHEMICAL CO., LTD.) and the like, (3) sodium carboxymethyl starch (e.g., manufactured by Matsutani Chemical Industry Co., Ltd.), (4) low-substituted hydroxypropylcellulose (e.g., manufactured by Shin-Etsu Chemical Co., Ltd.), (5) cornstarch and the like. The "crospovidone" may be any of the crosslinked polymer substances having a chemical name of 1-ethenyl-2-pyrrolidinone homopolymer, including those referred to as polyvinyl polypyrrolidone (PVPP), 1-vinyl-2-pyrrolidinone hornopolyxner. Specific examples include Kollidon CL (manufactured by BASF), Polyplasdon XL (manufactured by ISP), Polyplasdon XL-10 (manufactured by ISP), Polyplasdon INF-10 (manufactured by ISP) and the like.

Examples of the "water-soluble polymer" include ethanol-soluble water-soluble polymer [for example, cellulose derivatives such as hydroxypropylcellulose (hereinafter sometimes to be indicated as HPC) and the like, polyvinylpyrrolidone and the like], ethanol-insoluble water-soluble polymer [for example, cellulose derivatives such as hydroxypropylraethylcellulose (hereinafter sometimes to be indicated as HPMC), methylcellulose, sodium carboxymethylcellulose and the like, sodium polyacrylate, polyvinyl alcohol, sodium alginate, guar gum and the like] and the like.

Examples of the "basic inorganic salt" include basic inorganic salts of sodium, potassium, magnesium and/or calcium. Preferred is a basic inorganic salt, of magnesium and/or calcium. More preferred is a basic inorganic salt of magnesium. Examples of the basic inorganic salt of sodium include sodium carbonate, sodium hydrogen carbonate, disodium hydrogen phosphate and the like. Examples of the basic inorganic salt of potassium include potassium carbonate, potassium hydrogen carbonate and the like. Examples of the basic inorganic salt of magnesium include heavy magnesium carbonate, magnesium carbonate, magnesium oxide, magnesium hydroxide, magnesium aluminometasilicate, magnesium silicate, magnesium aluminate, synthetic hydrotalcite [$Mg_6Al_2(OH)_{15}.CO_3.4H_2O$] and aluminum magnesium hydroxide, preferably heavy magnesium carbonate, magnesium carbonate, magnesium oxide, magnesium hydroxide and the like. Examples of the basic inorganic salt of calcium include precipitated calcium carbonate, calcium hydroxide and the like.

Examples of the "solvent" include water for injection, alcohol, propylene glycol, Macrogol, sesame oil, corn oil, olive oil and the like.

Examples of the "solubilizing agent" include polyethylene glycol, propylene glycol, D-mannitol, benzyl benzoate, ethanol, trisaminomethane, cholesterol, triethanolamine, sodium carbonate, sodium citrate and the like.

Examples of the "suspending agent" include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the "isotonic agent" include glucose, D-sorbitol, sodium chloride, glycerin, D-mannitol and the like.

Examples of the "buffering agent" include buffer solutions such as phosphates, acetates, carbonates, citrates and the like.

Examples of the "soothing agent" include benzyl alcohol and the like.

Examples of the "preservative" include paraoxybenzoic acid esters, chlorobutanol, benzyl alcohol, phenethyl alcohol, dehydroacetic acid, sorbic acid and the like.

Examples of the "antioxidant" include sulfites, ascorbic acid, α-tocopherol and the like.

Examples of the "colorant" include Food dyes such as Food Yellow No. 5, Food Red No. 2, Food Blue No. 2 and the like; Food lake dyes, ferric oxide red and the like.

Examples of the "sweetening agent" include saccharin sodium, dipotassium glycyrrhizinate, aspartame, stevia, thaumatin and the like.

Examples of the "souring agent" include citric acid (citric anhydride), tartaric acid, malic acid and the like.

Examples of the "bubbling agent" include sodium bicarbonate and the like.

The "flavor" may be any of synthetic substances and naturally-occurring substances, and examples thereof include lemon, lime, orange, menthol, strawberry and the like.

Compound (VI) obtained by the method of the present invention can be formulated into a preparation for oral administration by a method known per se, by, for example, adding carriers such as excipient, disintegrant, binder, lubricant and the like, compression molding the mixture, and applying coating where necessary by a method known per se for the purpose of taste masking, enteric property or sustainability. When an enteric preparation is produced, an intermediate layer can also be formed by a method known per se between an enteric layer and a drug-containing layer to separate the both layers.

When compound (VI) obtained by the method of the present invention is formulated into, for example, an orally disintegrating tablet, for example, it can be produced by a method including coating a core containing crystalline cellulose and lactose with the compound (VI) and, where necessary, a basic inorganic salt, and further coating with a water-soluble polymer-containing coating layer to give a composition, coating the obtained composition with a polyethylene glycol-containing enteric coating layer, and then with a triethyl citrate-containing enteric coating layer, further coating with a polyethylene glycol-containing enteric coating layer, and finally coating with mannitol to give fine granules, mixing the obtained fine granules with an additive and molding the mixture.

Examples of the above-mentioned "enteric coating layer" include a layer composed of a mixture of one or more kinds from aqueous enteric polymer bases such as cellulose acetate phthalate (CAP), hydroxypropylmethylcellulose phthalate, hydroxyxnethylcellulose acetate succinate, methacrylic acid copolymer [for example, Eudragit L30D-55 (trade name; manufactured by Rohm), Colicoat MAE3QDP (trade name; manufactured by BASF), Polyquid PA30 (trade name; manufactured by Sanyo Chemical) and the like], carboxymethylethylcellulose, shellac and the like; sustained-release substrates such as methacrylic acid copolymer [for example, Eudragit NE30D (trade name), Eudragit RL30D (trade name), Eudragit RS30D (trade name) and the like] and the like; water-soluble polymer; plasticizer such as triethyl citrate, polyethylene glycol, acetylated monoglyceride, triacetin, castor oil and the like, and the like.

Examples of the above-mentioned "additive" include water-soluble sugar alcohols (e.g., sorbitol, mannitol and maltitol, reduced starch saccharides, xylitol, reduced paratinose, erythrltol etc.), crystalline cellulose (e.g., Ceolas KG 801, Avicel PH 101, Avicel PH 102, Avicel PH 301, Avicel PH 302, Avicel RC-591 (crystalline cellulose-carmellose sodium) etc.), low-substituted hydroxypropylcellulose (e.g., LH-22, LH-32, LH-23, LH-33 (Shin-Etsu Chemical Co., Ltd.) and a mixture of these etc.) and the like. Furthermore, binder, acidulant, bubbling agent, sweetening agent, flavor, lubricant, colorant, stabilizer, excipient, disintegrant and the like are also used.

Compound (VI) obtained, by the method of the present invention may be used in combination with 1 to 3 kinds of other active ingredients.

Examples of "other active ingredient" include anti-*Helicobacter pylori* active substance, imidazole compound, bismuth salt, quinoline compound and the like.

Examples of the "anti-*Helicobacter pylori* active substance" include penicillin antibiotics (e.g., amoxicillin, benzylpenicillin, piperacillin, mecillinam, ampicillin, temocillin, bacampicillin, aspoxicillin, sultamicillin, lenampicillin etc.), cephem antibiotics (e.g., cefixime, cefaclor etc.), macrolide antibiotics (e.g., erythromycin, clarithromycin, roxithromycin, rokitamycin, flurithromycin, telithromycin etc.), tetracycline antibiotics (e.g., tetracycline, minocycline, streptomycin etc.), aminoglycoside antibiotics (e.g., gentamicin, amikacin etc.), imipenem and the like. Of these, penicillin antibiotic, macrolide antibiotic and the like are preferable.

Examples of the "imidazole compound" include metronidazole, miconazole, tinidazole and the like.

Examples of the "bismuth salt" include bismuth acetate, bismuth citrate, bismuth subsalicylate and the like.

Examples of the "quinolone compound" include ofloxacin, ciploxacin, sitafloxacin and the like.

Particularly, for eradication of *Helicobacter pylori*, compound (VI) obtained by the method of the present invention or a salt thereof, and penicillin antibiotics (e.g., amoxicillin etc.) and erythromycin antibiotics (e.g., clarithromycin etc.) are preferably used. In other embodiments, (i) compound (VI) obtained by the method of the present invention or a salt thereof, and penicillin antibiotics (e.g., amoxicillin etc.), (ii) compound (VI) obtained by the method of the present invention or a salt, thereof, and penicillin antibiotics (e.g., amoxicillin etc.) and imidazole compounds (e.g., metronidazole etc.), (iii) compound (VI) obtained by the method of the present invention or a salt thereof, and penicillin antibiotics (e.g., amoxicillin etc.) and quinoline compounds (e.g., sitafloxacin etc.) are preferably used. For eradication of *Helicobacter pylori*, such combination therapy is consecutively used for about 5 days to 14 days, preferably 7 days.

For eradication of *Helicobacter pylori*, compound (VI) obtained by the method of the present invention singly has an anti-*Helicobacter pylori* action (bacteriostatic action or eradication action). Its intragastric pH-regulating action and the like can enhance an antibacterial action of other antibiotics, and also provides an eradication effect-aiding action based on the action, of an antibiotic to be used in combination.

Also, compound (VI) obtained by the method of the present invention may be used in combination with a gastric motility enhancer, a drug acting on lower esophageal sphincter (e.g., temporary lower esophageal sphincter relaxation suppressant etc.), a ClC-2 channel opener (intestinal juice secretion enhancer), a histamine H2 receptor antagonist, an antacid, a sedative, a stomachic digestant or a non-steroidal anti-inflammatory agent (NSAID).

Examples of the "gastric motility enhancer" include domperidone, metoclopramide, mosapride, itopride, tegaserod, acotiamide and the like.

Examples of the "drug acting on lower esophageal, sphincter" include GABA-B receptor agonists such as baclofen, an optically active form thereof and the like, and the like.

Examples of the "ClC-2 channel opener (intestinal juice secretion enhancer)" include lubiprostone and the like.

Examples of the "histamine H2 receptor antagonist" include cimetidine, ranitidine, famotidine, roxatidine, nizatidine, lafutidine and the like.

Examples of the "antacid" include sodium hydrogen carbonate, aluminum hydroxide and the like.

Examples of the "sedative" include diazepam, chlordiazepoxide and the like.

Examples of the "stomachic digestant" include *Gentiana lutea*, swertia kaponica, diastase and the like.

Examples of the "non-steroidal anti-inflammatory agent" include aspirin, indomethacin, ibuprofen, mefenamic acid, diclofenac, etodolac, piroxicam, celecoxib and the like.

A gastric motility enhancer, a drug acting on lower esophageal sphincter, a ClC-2 channel opener (intestinal juice secretion enhancer), a histamine H2 receptor antagonist, an antacid, a sedative, a stomachic digestant or non-steroidal anti-inflammatory agent may be mixed with compound (VI) obtained by the method of the present invention or a salt thereof by a method known per se, formulated into a single pharmaceutical composition (e.g., tablet, powder, granule, capsule (including soft capsule), liquid, injection, suppository, sustained-release preparation etc.) and used in combination, or they may be formulated separately, and administered to the same subject simultaneously or in a staggered manner.

Compound (VI) obtained by the method of the present invention may also be used in combination with the following medicaments.

(i) proton pump inhibitors, for example, omeprazole, esomeprazole, pantoprazole, rabeprazole, tenatoprazole, ilaprazole and lansoprazole;

(ii) oral antacid mixtures, for example, Maalox (registered trade mark), Aludrox (registered trade mark) and Gaviscon (registered trade mark);

(iii) mucosal protective agents, for example, polaprezinc, ecabet sodium, rebamipide, teprenone, cetraxate, sucralfate, chloropylline-copper and plaunotol;

(iv) anti-gastric agents, for example, anti-gastrin vaccine, itriglumide and Z-360;

(v) 5-HT3 antagonists, for example, dolasetron, palonosetron, alosetron, azasetron, ramosetron, mitrazapine, granisetron, tropisetron, E-3620, ondansetron and indisetron;

(vi) 5-HT4 agonists, for example, tegaserod, mosapride, cinitapride and oxtriptane;

(vii) laxatives, for example, Trifyba (registered trade mark), Fybogel (registered trade mark), Konsyl (registered trade mark), Isogel (registered trade mark), Regulan (registered trade mark), Celevac (registered trade mark) and Normacol (registered trade mark);

(viii) GABAB agonists, for example, baclofen and AZD-3355;

(ix) GABAB antagonists, for example, GAS-360 and SGS-742;

(x) calcium channel blockers, for example, aranidipine, lacidipine, falodipine, azelnidipine, clinidipine, lomerizine, diltiazem, gallopamil, efonidipine, nisoldipine, amlodipine, lercanidipine, bevantolol, nicardipine, isradipine, benidipine, verapamil, nitrendipine, barnidipine, propafenone, manidipine, bepridil, nifedipine, nilvadipine, nimodipine and fasudil;

(xi) dopamine antagonists, for example, metoclopramide, domperidone and levosulpiride;

(xii) tachykinin (NK) antagonists, particularly, NK-3, NK-2 and NK-1 antagonists, for example, nepadutant, saredutant, talnetant, (αR, 9R)-7-[3,5-bis(trifluoromethyl)benzyl]-8,9,10,11-tetrahydro-9-methyl-5-(4-methylphenyl)-7H-[1,4]diazocino[2,1-g] [1,7]naphthyridine-6-13-dione (TAK-637), 5-[(2R,3S)-2-[(1R)-1-[3,5-bis(trifluoromethyl)phenyl]ethoxy-3-(4-fluorophenyl)-4-morpholinyl]methyl]-1,2-dihydro-3H-1,2,4-triazol-3-one (MK-869), lanepitant, dapitant and 3-[[2-methoxy-5-(trifluoromethoxy)phenyl]methylamino]-2-phenyl-piperidine(2S,3S);

(xiii) nitric oxide synthase inhibitors, for example, GW-274150, tilarginine, P54, guanidioethyldisulfide and nitroflurbiprofen;

(xiv) vanilloid receptor 1 antagonists, for example, AMG-517 and GW-705498;

(xv) ghrelin agonists, for example, capromorelin and TZP-101;

(xvi) AchE release stimulants, for example, Z-338 and KW-5092;

(xvii) antiplatelet agents, for example, ticlopidine, clopidogrel, prasugrel, low-dose aspirin and the like.

The above-mentioned medicaments may be mixed with compound (VI) obtained by the method of the present invention or a salt thereof by a method known per se, formulated into a single pharmaceutical composition (e.g., tablet, powder, granule, capsule (including soft capsule), liquid, injection, suppository, sustained-release preparation etc.) and used in combination, or they may be formulated separately, and administered to the same subject simultaneously or in a staggered manner. They can be safely administered orally or parenterally (e.g., topical, rectal, intravenous etc.). Particularly, they are preferably administered orally as tablet, granule, capsule and the like. These administration forms are collectively abbreviated in the following as the combination agent of the present invention.

The combination agent of the present invention has low toxicity, and the concomitant drug and compound (VI) may be simultaneously administered, or compound (VI) may be administered after administration of the concomitant drug, or the concomitant drug may be administered after administration of compound (VI). In case of staggered administration, the time interval varies depending on the active ingredients to be administered, a formulation and an administration route. For example, when the concomitant drugs are administered first, compound (VI) may be administered 1 min to 3 days, preferably 10 min to 1 day, more preferably 15 min to 1 hr after administering the concomitant drugs. When compound (VI) obtained by the method of the present invention is administered first, the concomitant drugs may be administered 1 min to 1 day, preferably 10 min to 6 hr, more preferably 15 min to 1 hr after administering compound (VI).

As long as the side effects do not pose problems, any amount of the concomitant drug can be adopted. While the daily dose of the concomitant drug varies depending on the dose, administration subject, administration route, target disease, symptom and the like, for example, when an anti-ulcer agent is orally administered to an adult (body weight about 60 kg), it is, for example, about 0.5-about 1500 mg/kg body weight/day, preferably about 5-about 150 mg/kg body weight/day, of the active ingredient. The dose may be administered once per day or in 2-3 portions per day.

When compound (VI) is used in combination with a concomitant drug, the dose of each medicament can be reduced within the safe range in consideration of counter effects of the medicaments.

As a pharmacologically acceptable carrier which can be used for the production of the combination agent of the present invention, those similar to the carriers used for the above-mentioned pharmaceutical composition containing compound (VI) can be used.

Two or more kinds of the above-mentioned concomitant drug may be used in combination at an appropriate ratio.

The dose of the concomitant drug can be appropriately determined with the clinically-used dose as the standard. In addition, the mixing ratio of compound (VI) obtained by the method of the present invention and the concomitant drug can be appropriately determined according to the administration subject, administration route, target disease, symptom, combination and the like. For example, when the administration subject is human, 0.01-100 parts by weight of the concomitant drug can be used per 100 parts by weight of compound (VI).

For example, the content of compound (VI) in the combination agent of the present invention differs depending on the form of a preparation, and usually in the range from about 0.01 to 99.9 wt %, preferably in the range from about 0.1 to 50 wt %, further preferably in the range from about 0.5 to 20 wt %, based on the whole preparation.

The content of the concomitant drug in the combination agent of the present invention differs depending on the forms of the preparation, and usually in the range from about 0.01 to 99.9 wt %, preferably in the range from about 0.1 to about 50 wt %, further preferably in the range from about 0.5 to about 20 wt %, based on the whole preparation.

The content of additives such as a carrier and the like in the combination agent of the present invention differs depending on the form of a preparation, and usually in the range from about 1 to 99.99 wt %, preferably in the range from about 10 to about 90 wt %, based on the whole preparation.

When compound (VI) and a concomitant drug are separately formulated into preparations, similar contents can be used.

Since the dosage as described above varies depending on various conditions, amounts smaller than the above-mentioned dosage may sometimes be sufficient, further, amounts over the above-mentioned range sometimes have to be administered.

EXAMPLES

The present invention is further explained concretely in the following by referring to Reference Examples and Examples, which are not to be construed as limitative.

In the following Reference Examples and Examples, "room temperature" generally shows about 10° C. to about 35° C., but is not particularly strictly limited. The mixing ratio of liquids is in a volume ratio. Unless particularly indicated, "%" shows weight percentage. The yield shows mol/mol %. $^1$H-NMR spectrum was measured by Bruker AVANCE III500 (500 MHz) by using tetramethylsilane as the internal standard.

Abbreviations in Examples and Reference Examples mean the following.

s: singlet, d: doublet, dd: double doublet, dad: double double doublet, m: multiplet, brs: broad, singlet, J: coupling constant, Hz: Hertz.

Reference Example 1 (Toluene Solvent)

Pyridine-3-sulfonyl Chloride

Pyridine-3-sulfonic acid (2.00 g, 12.6 mmol) and phosphorus pentachloride (3.14 g, 15.1 mmol) were suspended in toluene (3 mL) at room temperature. After stirring under reflux for about 3 hr, the mixture was cooled to room temperature. Toluene (10 mL) and water (6 mL) were added into another kolben, and the mixture was cooled to an inside temperature of 5±5° C. The reaction solution was added dropwise at not more than an inside temperature of 25° C., and washed well with toluene (2 mL). After cooling to an inside temperature of 5±5° C., 50% aqueous potassium carbonate solution (about 6.4 mL) was added dropwise at not more than an inside temperature of 10° C., and the mixture was adjusted to pH 7.0±0.5. Under ice-cooling, and the mixture was stirred for 30 min, toluene (4 mL) and water (4 mL) were added and the mixture was partitioned. The organic layer was washed with saturated brine (10 mL) and concentrated under reduced pressure. Toluene (5 mL) was added and the mixture was concentrated again, which operation was repeated twice to give a toluene solution of pyridine-3-sulfonyl chloride (quantified yield 1.69 g, 75.6%, total, amount 2.14 g, 79.0 w/w % toluene solution).

Example 1 (Chlorobenzene Solvent)

5-(2-fluorophenyl)-1-(pyridin-3-ylsulfonyl)-1H-pyrrole-3-carbaldehyde

Pyridine-3-sulfonic acid (10.7 g, 68.5 mmol) and phosphorus pentachloride (15.7 g, 75.4 mmol) were suspended in chlorobenzene (15 mL) at room temperature. After heating and stirring at an inside temperature of 105±5° C. for about 3 hr, the mixture was cooled to room temperature. Toluene (50 mL) and water (30 mL) were added into another kolben, and the mixture was cooled to an inside temperature of 5±5° C. The reaction solution was added dropwise at not more than an inside temperature of 15° C., and the dropping funnel was washed well with a mixed solution of toluene and water (1:1, 20 mL). After cooling to an inside temperature of 5±5° C., 50% aqueous potassium carbonate solution (39 mL) was added dropwise at not more than an inside temperature of 20° C., and the mixture was adjusted to pH 7.5±0.5. After partitioning at room temperature, the organic layer was washed with 5% brine (40 mL), and concentrated to about 20 mL under reduced pressure. Toluene (40 mL) was added and the mixture was concentrated again to about 20 mL. An operation of adding acetonitrile (40 mL) and concentrating the mixture to about 20 mL was repeated three times to give an acetonitrile solution of pyridine-3-sulfonylchloride (quantified, yield 10.7 g, 87.9%, total amount 20.3 g, 52.7 w/w % acetonitrile solution).

To the acetonitrile solution (total amount) of pyridine-3-sulfonylchloride obtained above were added acetonitrile (45 mL), 5-(2-fluorophenyl)-1H-pyrrole-3-carbaldehyde (10.0 g, 52.9 mmol), N,N-dimethylpyridin-4-amine (0.646 g, 5.29 mmol) and triethylamine (10.4 mL, 74.1 mmol), and the mixture was heated to an inside temperature of 4 5±5° C. After stirring at an inside temperature of 45±5° C. for 1.5 hr, the mixture was cooled to room temperature, and water (30 mL) was added dropwise. The mixture was adjusted to pH 4-5 with 0.5M hydrochloric acid (about 20 mL). The seed crystal of the title compound was added and, after confirmation of crystal precipitation, water (60 mL) was added dropwise. After stirring at room temperature for 30 min and at 5±5° C. for 1 hr, the precipitated crystals were collected by filtration. The crystals were washed twice with a mixed solution of acetonitrile and water (1:2, 30 mL) cooled to 5±5° C. in advance, and dried at an outer temperature of 50° C. under reduced pressure to give the title compound (15.5 g, isolation yield 88.7%).

$^1$H NMR (500 MHz, CDCl$_3$) δ 6.68 (d, J=1.6 Hz, 1H), 7.02 (dd, J=8.2, 8.2 Hz, 1H), 7.14-7.19 (m, 2H), 7.38 (dd, J=8.2, 4.9 Hz, 1H), 7.44-7.48 (m, 1H), 7.72 (ddd, J=8.2, 2.5, 1.6 Hz, 1H), 8.17 (d, J=1.9 Hz, 1H), 8.59 (d, J=1.9 Hz, 1H), 8.82 (dd, J=4.7, 1.6 Hz, 1H), 9.90 (s, 1H).

Example 2

1-[5-(2-fluorophenyl)-1-(pyridin-3-ylsulfonyl)-1H-pyrrol-3-yl]-N-methylmethanamine fumarate N,N-dimethylacetamide (18 mL) and sodium borohydride (0.550 g, 14.5 mmol) were added into a nitrogen-substituted kolben and dissolved therein (solution A). Into another nitrogen-substituted kolben were added 5-(2-fluorophenyl)-1-(pyridin-3-ylsulfonyl)-1H-pyrrole-3-carbaldehyde (10.0 g, 30.3 mmol) and methanol (50 mL), a 40% solution of methylamine in methanol (3.30 g, 42.5 mmol) was sequentially added dropwise at room temperature, and the mixture was stirred at room temperature for 1 hr. The mixture was cooled to an inside temperature of 5° C., solution A prepared in advance was added dropwise at an inside temperature of 5±5° C., and washed well with N,N-dimethylacetamide (2 mL). The mixture was stirred at an inside temperature of 5±5° C. for 1 hr. 1M hydrochloric acid (70 mL) was added dropwise at not more than an inside temperature of 20° C., and the mixture was stirred at an inside temperature of 20±5° C. for 30 rain. 12.5% Aqueous ammonia (60 mL) and ethyl acetate (100 mL) were added to partition the solution. The aqueous layer was extracted with 5% brine (50 mL) and ethyl acetate (50 mL). The combined organic layer was washed twice with 5% brine (60 mL). The organic layer was concentrated to about 25 mL, ethyl acetate (70 mL) was added, and the mixture was concentrated again to about 38 mL. N,N-dimethylacetamide (60 mL) was added, the mixture was heated to an inside temperature of 45° C., and fumaric acid (3.52 g, 30.3 mmol) was added. After stirring at an inside temperature of 45±5° C. for 30 min, ethyl acetate (30 mL) was added dropwise, and the mixture was stirred at an inside temperature of 45±5° C. for 30 min. After cooling, the mixture was stirred at room temperature for 1 hr. The precipitated crystals were collected by filtration. The crystals were washed with a mixed solution of ethyl acetate and N,N-dimethylacetamide (1:1, 15 mL), and then with ethyl acetate (30 ml) to give a crude product (wet form).

The crude product obtained above (wet form, total amount) was suspended in a mixed solution of methanol and water (2:3, 174 mL) at room temperature, and dissolved at an inside temperature of 65±5° C. Activated carbon SHIRASAGI A (registered trade mark) (0.340 g) was added, and the mixture was stirred for 1.5 hr and filtered. The filtered activated carbon was washed with a mixed solution of methanol and water (2:3, 18 mL). The combined filtrate was re-dissolved at an inside temperature of 65±5° C., cooled to room temperature, and further stirred at an inside temperature of 5±5° C. for 1 hr. The precipitated crystals were collected by filtration. The crystals were washed with a mixed solution of methanol and water (2:3, 23 mL), dried at an outer temperature of 50° C. under reduced pressure to give the title compound (10.5 g, isolation yield 75.2%).

$^1$H NMR (500 MHz, DMSO-d$_6$) δ 2.48 (s, 3H), 3.95 (s, 2H), 6.51 (s, 2H), 6.53 (d, J=1.6 Hz, 1H), 7.09-7.12 (m, 1H), 7.21-7.25 (m, 2H), 7.51-7.55 (m, 1H), 7.62 (dd, J=8.2, 5.0 Hz, 1H), 7.80 (brs, 1H), 7.90 (add, J=8.2, 2.5, 1.6 Hz, 1H), 8.57 (d, J=1.9 Hz, 1H), 8.89 (dd, J=4.7, 1.6 Hz, 1H), 10.53 (brs, 3H).

Example 3 (Trifluoromethylbenzene Solvent)

5-(2-fluorophenyl)-1-(pyridin-3-ylsulfonyl)-1H-pyrrole-3-carbaldehyde

Pyridine-3-sulfonic acid (3.00 g, 18.8 mmol) and phosphorus pentachloride (4.31 g, 20.7 mmol) were suspended in trifluoromethylbenzene (4.5 mL) at room temperature. After stirring under reflux for about 3 hr, the mixture was cooled to room temperature. Ethyl acetate (15 mL) and water (9 mL) were added into another kolben, and the mixture was cooled to an inside temperature of 5±5° C. The reaction solution was added dropwise at not more than an inside temperature of 25° C., and washed well with a mixed solution of ethyl acetate and water (1:1, 6 mL). After cooling to an inside temperature of 5±5° C., the mixture was adjusted to pH 7.5±0.5 by adding 50% aqueous potassium carbonate solution (9.5 mL) dropwise at not more than an inside temperature of 20° C. After partitioning at room temperature, the organic layer was washed with 10% brine (15 mL), and concentrated under reduced pressure. An operation of adding ethyl acetate (12 mL) to the concentrated residue and concentrating the mixture was repeated twice and an operation of adding acetonitrile (12 mL) and concentrating the mixture again was repeated twice to give pyridine-3-sulfonyl chloride as an oil (quantified yield 2.74 g, 81.9%).

To the pyridine-3-sulfonyl chloride (1.03 g, 5.80 mmol) obtained above were added acetonitrile (5 mL), 5-(2-fluorophenyl)-1H-pyrrole-3-carbaldehyde (1.00 g, 5.29 mmol), N,N-dimethylpyridin-4-amine (65.0 mg, 0.532 mmol) and triethylamine (1.04 mL, 7.41 mmol), and the mixture was heated to an inside temperature of 45±5° C. After stirring at an inside temperature of 45±5° C. for 1.5 hr, the mixture was cooled to room temperature. Water (3 mL) was added dropwise, and the mixture was adjusted to pH 4-5 with 0.5M hydrochloric acid (about 2.5 mL). After confirmation of crystal precipitation, water (4.5 mL) was added dropwise. After stirring at room temperature for 30 min and at 5±5° C. for 1 hr, the precipitated crystals were collected by filtration. The crystals were washed twice with a mixed solution of acetonitrile and water (1:2, 3 mL) cooled, to 5±5° C. in advance, and dried at an outer temperature of 50° C. under reduced pressure to give the title compound (1.51 g, isolation yield 86.4%).

Formulation Examples of compound (VI) obtained by the method of the present invention are shown below.

Preparation Example 1

An uncoated tablet (core tablet) containing 1-[5-(2-fluorophenyl)-1-(pyridin-3-ylsulfonyl)-1H-pyrrol-3-yl]-N-methylmethanamine fumarate (hereinafter to be referred to as compound A) was produced as follows at a composition ratio shown in Table 1. That is, compound A (8596 g, content correction), D-mannitol (48090 g, weight correction) and crystalline cellulose (7007 g) were charged in a fluid bed dryer granulator (model FD-WSG-60 manufactured by POWREX), preheated and mixed. Hydroxypropylcellulose (2402 g, overage) and fumaric acid (80.07 g, overage) were dissolved in purified water (37.6 L, overage) and the aqueous solution (35129 g) was sprayed to give a granulated powder. The obtained granulated powder (63450 g) was passed through a power mill (model P-7S manufactured by SHOWA KAGAKU KIKAI CO., LTD.) to give a sieved powder. The sieved powder (62390 g), croscarmellose sodium (3319 g) and magnesium stearate (663.7 g) were charged in a tumbler mixer (model TM-400S manufactured by SHOWA KAGAKU KIKAI CO., LTD.), and mixed to give a mixed powder. The mixed powder was tableted by a rotary tableting machine (model AQU31029SW4JII manufactured by Kikusui Seisakusho Ltd.) with a pestle (8×4.5 mm) at 110 mg/tablet to give uncoated tablets (core tablets).
[Table 1]
<Composition of Uncoated Tablet (Core Tablet) Containing Compound A>
Compound A 13.36 mg
D-mannitol 75.63 mg
crystalline cellulose 11 mg
hydroxypropylcellulose 3.3 mg
fumaric acid 0.11 mg
croscarmellose sodium 5.5 mg
magnesium stearate 1.1 mg
Total 110 mg The obtained uncoated tablets (core tablets, 59400 g) were placed in a film coating machine (model DRC-1200DS manufactured by POWREX), a coating solution (29892 g) at the composition ratio shown in Table 2 was sprayed. Then, a coating solution (324 g) at the composition ratio shown in Table 3 was sprayed to give quick-integrating tablets (about 114.5975 mg/tablet).
[Table 2]
<Composition of Coating Solution>
hypromellose 3.375 mg
Macrogol 6000 0.75 mg
titanium oxide 0.375 mg
yellow ferric oxide 0.0375 mg
purified water 40.8375 mg
Total (solid content) 45.375 (4.5375) mg
[Table 3]
<Composition of Coating Solution>
Macrogol 6000 0.06 mg
purified water 0.54 mg
Total (solid content) 0.6 (0.06) mg Preparation Example 2

The film-coated tablets (32890 g) obtained in Preparation Example 1 were printed with an ink solution at a composition ratio shown in Table 4 and diluted with n-butanol to a viscosity of 40-55 mPas by a tablet imprinting machine (QI-300 model manufactured by Qualicaps Co., Ltd.) to give printed tablets.
[Table 4]
<Composition of Ink Solution>
white shellac 26.0%
black iron oxide 10.0%
anhydrous ethanol 26.0%
1-butanol 38.0%

Preparation Example 3

An uncoated tablet (core tablet) containing compound A was produced as follows at a composition ratio shown in Table 5. That is, compound A (8596 g, content correction), D-mannitol (48090 g, weight correction) and crystalline cellulose (7007 g) were charged in a fluid bed dryer granulator (model FD-WSG-60 manufactured by POWREX), preheated and mixed. Hydroxypropylcellulose (2402 g, overage) and fumaric acid (80.07 g, overage) were dissolved in purified water (37.6 L, overage) and the aqueous solution (35073 g) was sprayed to give a granulated powder. The obtained granulated powder (63450 g) was passed through a power mill (P-7S model manufactured by SHOWA KAGAKU KIKAI CO., LTD.) to give a sieved powder. The sieved powder (62390 g), croscarmellose sodium (3319 g) and magnesium stearate (663.7 g) were charged in a tumbler mixer (model TM-400S manufactured by SHOWA KAGAKU KIKAI CO., LTD.), and mixed to give a mixed powder. The mixed powder was tableted by a rotary tableting machine (model AQU31029SW4JII manufactured by Kikusui Seisakusho Ltd.) with a pestle (11×6 mm) at 220 mg/tablet to give uncoated tablets (core tablets).

[Table 5]
<Composition of Uncoated Tablet (Core Tablet) Containing Compound A>
Compound A 26.72 mg
D-mannitol 151.26 mg
crystalline cellulose 22 mg
hydroxypropylcellulose 6.6 mg
fumaric acid 0.22 mg
croscarmellose sodium 11 mg
magnesium stearate 2.2 mg
Total 220 mg The obtained uncoated tablets (core tablets, 59400 g) were placed in a film coating machine (model DRC-1200DS manufactured by POWREX), a coating solution (27838 g) at the composition ratio shown in Table 6 was sprayed. Then, a coating solution (270 g) at the composition ratio shown in Table 7 was sprayed to give quick-integrating tablets (about 229.115 mg/tablet).

[Table 6]
<Composition of Coating Solution>
hypromellose 6.75 mg
Macrogol 6000 1.5 mg
titanium oxide 0.75 mg
red ferric oxide 0.015 mg
purified water 81.135 mg
Total (solid content) 90.15 (9.015) mg

[Table 7]
<Composition of Coating Solution>
Macrogol 6000 0.1 mg
purified water 0.9 mg
Total (solid content) 0.1 (1.0) mg Preparation Example 4

The film-coated tablets (53380 g) obtained in Preparation Example 3 were printed with an ink solution at a composition ratio shown in Table 4 and diluted with n-butanol to a viscosity of 40-55 mPas by a tablet imprinting machine (QI-300 model manufactured by Qualicaps Co., Ltd.) to give printed tablets.

INDUSTRIAL APPLICABILITY

According to the present invention, since the reaction of a pyridine-3-sulfonic acid compound and phosphorus pentachloride to give a pyridine-3-sulfonyl chloride compound is performed in a solvent of chlorobenzene or trifluoromethylbenzene, the pyridine-3-sulfonyl chloride compound can be produced more conveniently and more efficiently. Also, the present invention is useful since the production cost of the pyrrole compound can be reduced by the use of a pyridine-3-sulfonyl chloride compound obtained by the production method.

This application is based on patent application No. 2013-039809 filed in Japan, the contents of which are encompassed in full herein.

The invention claimed is:

1. A production method of a compound represented by the formula (VI):

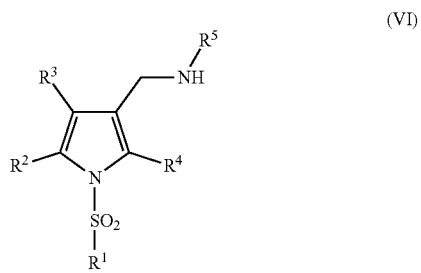

wherein
R$^1$ is a pyridin-3-yl group optionally substituted by 1 to 3 substituents selected from (i) halogen, (ii) cyano, (iii) C$_{1-6}$ alkyl optionally substituted by 1-5 halogens, (iv) C$_{1-6}$ alkoxy optionally substituted by 1-5 halogens, (v) an amino group optionally substituted by C$_{1-6}$ alkyl and (vi) C$_{1-6}$ alkoxy-carbonyl,
R$^2$ is
(a) a C$_{6-14}$ aryl group optionally substituted by 1-5 substituents selected from (i) a halogen atom, (ii) cyano, (iii) C$_{1-6}$ alkyl optionally substituted by 1-5 halogens, (iv) C$_{1-6}$ alkoxy optionally substituted by 1-5 halogens, (v) acetyl, (vi) C$_{3-7}$ cycloalkyl, (vii) C$_{1-6}$ alkylsulfonyl, (viii) C$_{1-6}$ alkylthio optionally substituted by 1-5 halogens and (ix) C$_{1-6}$ alkylsulfinyl,
(b) a thienyl group optionally substituted by 1 to 3 substituents selected from (i) a halogen atom, (ii) cyano, (iii) C$_{1-6}$ alkyl optionally substituted by 1-5 halogens, (iv) C$_{1-6}$ alkoxy optionally substituted by 1-5 halogens and (v) acetyl, or
(c) a pyridyl group optionally substituted by 1 to 4 substituents selected from (i) a halogen atom, (ii) cyano, (iii) C$_{1-6}$ alkyl optionally substituted by 1-5 halogens, (iv) C$_{1-6}$ alkoxy optionally substituted 1-5 halogens, (v) acetyl and (vi) nitro,
R$^3$ and R$^4$ are each independently a hydrogen atom, a C$_{1-6}$ alkyl group, a C$_{1-6}$ alkyl-carbonyl group, a fluorine atom or a chlorine atom,
and R$^5$ is an alkyl group or a salt thereof,
comprising reacting, without isolation, the pyridine-3-sulfonyl chloride compound represented by the following formula (II):

wherein R$^1$ is as defined above, which is obtained by reacting a pyridine-3-sulfonic acid compound with phosphorus pentachloride in a solvent of chlorobenzene or trifluoromethylbenzene,
with a compound represented by the formula (III):

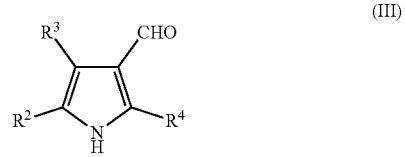

wherein each symbol is as defined above, or a salt thereof to produce a compound represented by the formula (IV):

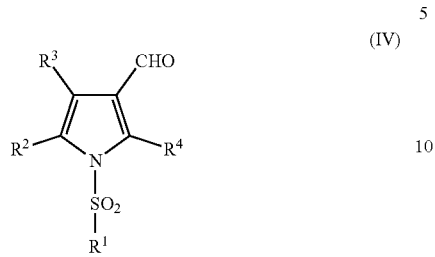

wherein each symbol is as defined above,
or a salt thereof, and reacting the compound with a compound represented by the formula (V):

wherein $R^5$ is as defined above, or a salt thereof in the presence of a reducing agent.

2. The production method according to claim 1, wherein $R^1$ is an unsubstituted pyridin-3-yl group,
$R^2$ is a 2-fluorophenyl group,
$R^3$ and $R^4$ are each a hydrogen atom, and
$R^5$ is a methyl group.

* * * * *